(12) United States Patent
Sun et al.

(10) Patent No.: US 12,121,752 B2
(45) Date of Patent: Oct. 22, 2024

(54) SYSTEMS AND METHODS FOR RADIATION THERAPY

(71) Applicant: SHANGHAI UNITED IMAGING HEALTHCARE CO., LTD., Shanghai (CN)

(72) Inventors: Buliang Sun, Shanghai (CN); Can Liao, Shanghai (CN); Bo Cai, Shanghai (CN); Zhidu Zhang, Shanghai (CN); Hanyi Zhang, Shanghai (CN); Wei Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 237 days.

(21) Appl. No.: 17/929,681

(22) Filed: Sep. 2, 2022

(65) Prior Publication Data
US 2023/0076168 A1 Mar. 9, 2023

(30) Foreign Application Priority Data

Sep. 3, 2021 (CN) .......................... 202111031794.4
Dec. 31, 2021 (CN) .......................... 202111672121.7

(51) Int. Cl.
*A61N 5/10* (2006.01)
*G06T 7/00* (2017.01)
*G06T 7/246* (2017.01)

(52) U.S. Cl.
CPC .......... *A61N 5/107* (2013.01); *A61N 5/1049* (2013.01); *G06T 7/0016* (2013.01); *G06T 7/248* (2017.01); *G06T 2207/30076* (2013.01)

(58) Field of Classification Search
CPC .... A61N 5/107; A61N 5/1049; A61N 5/1068; A61N 5/1069; A61N 2005/1059; A61N 5/1067; A61N 5/1071; G06T 7/0016; G06T 7/248; G06T 2207/30076
See application file for complete search history.

(56) References Cited

U.S. PATENT DOCUMENTS

2014/0343344 A1* 11/2014 Saunders ............. A61N 5/1049
                                                                 600/1
2015/0016586 A1*  1/2015 Maurer, Jr. ........... G06T 7/0014
                                                                  378/5

FOREIGN PATENT DOCUMENTS

CN           105031833 A      11/2015

* cited by examiner

*Primary Examiner* — Kiho Kim
(74) *Attorney, Agent, or Firm* — METIS IP LLC

(57) ABSTRACT

The present disclosure is related to systems and methods for radiation. The method may include obtaining a plurality of reference images of a target of a subject and reference physiological motion information of the subject. The plurality of reference images and the reference physiological motion information may be acquired in a radiation period. The method may include establishing a correlation model based on the plurality of reference images and the reference physiological motion information. The method may include monitoring real-time motion information of the target based on the correlation model during a radiation operation performed during the radiation period.

20 Claims, 14 Drawing Sheets

400

| Obtaining a plurality of reference images of a target of a subject and reference physiological motion information of the subject, wherein the plurality of reference images and the reference physiological motion information are acquired in a radiation period | ~ 410 |

↓

| Establishing a correlation model based on the plurality of reference images and the reference physiological motion information | ~ 420 |

↓

| Monitoring real-time motion information of the target based on the correlation model during a radiation operation performed during the radiation period | ~ 430 |

FIG. 4

SYSTEMS AND METHODS FOR RADIATION THERAPY

CROSS-REFERENCE TO RELATED APPLICATIONS

This application claims priority of Chinese Patent Application No. 202111672121.7, filed on Dec. 31, 2021, and Chinese Patent Application No. 202111031794.4, filed on Sep. 3, 2021, the contents of each of which are hereby incorporated by reference.

TECHNICAL FIELD

The present disclosure generally relates to radiation therapy, and more particularly, to systems and methods for motion monitoring and radiation dose verification in radiation therapy.

BACKGROUND

Radiation therapy (RT) is widely used in clinical treatment (e.g., tumor therapy). During the radiation therapy, a motion (e.g., a physiological motion) of a patient may occur and may affect the radiation therapy process. Further, after the radiation therapy is completed, it is often necessary to verify a radiation dose distribution in the body of the patient to determine whether a tumor area receives a planning radiation dose, where the motion of the patient may also affect the accuracy of the dose verification. Thus, it is desirable to provide systems and methods for motion monitoring and radiation dose verification in radiation therapy.

SUMMARY

According to an aspect of the present disclosure, a radiation system may include at least one storage medium including a set of instructions, and at least one processor in communication with the at least one storage medium. When executing the set of instructions, the at least one processor may be directed to cause the system to perform a method. The method may include obtaining a plurality of reference images of a target of a subject and reference physiological motion information of the subject. The plurality of reference images and the reference physiological motion information may be acquired in a radiation period. The method may include establishing a correlation model based on the plurality of reference images and the reference physiological motion information. The method may include monitoring real-time motion information of the target based on the correlation model during a radiation operation performed during the radiation period.

In some embodiments, the method may include obtaining a positioning reference image of the subject. The method may include obtaining a plurality of candidate images of the target of the subject. The method may include determining the plurality of reference images of the target by combining the plurality of candidate images of the target and the positioning reference image of the subject.

In some embodiments, the reference physiological motion information may include a respiratory signal or an image feature related to a respiratory motion of the subject.

In some embodiments, the correlation model may reflect a relationship between the plurality of reference images and phases of the reference physiological motion information respectively.

In some embodiments, the method may include obtaining a target image of the subject acquired during the radiation operation and corresponding target physiological motion information of the subject. The method may include determining a target phase based on the target physiological motion information. The method may include obtaining a target reference image based on the target phase and the correlation model. The method may include monitoring the real-time motion information of the target by comparing the target reference image and the target image.

In some embodiments, the method may include adjusting at least one parameter associated with the radiation operation based on the real-time motion information of the target.

In some embodiments, the plurality of reference images of the target may be acquired by an imaging device online before the radiation operation. The plurality of reference images may correspond to different time points in the radiation period.

In some embodiments, the method may include obtaining a target image of the subject acquired during the radiation operation and corresponding target physiological motion information of the subject. The method may include dividing the target image into a plurality of groups of sub-target images based on the target physiological motion information. The plurality of groups of sub-target images may correspond to a plurality of phases of the target physiological motion information. The method may include, for each group of the plurality of groups of sub-target images, obtaining a group of sub-verification images corresponding to the group of sub-target images. The group of sub-verification images and the group of sub-target images may correspond to a same phase. The method may include determining a sub-dose field based on the group of sub-target images and the group of sub-verification images. The method may include determining a target dose field corresponding to the target image based on a plurality of sub-dose fields corresponding to the plurality of groups of sub-target images.

In some embodiments, the group of sub-verification images corresponding to the group of sub-target images may be obtained by dividing a verification image. The verification image may include at least one of a treatment planning image, an image acquired before the radiation operation, or an image acquired during the radiation operation.

In some embodiments, the method may include determining the target dose field by combining the plurality of sub-dose fields corresponding to the plurality of groups of sub-target images.

In some embodiments, the method may include, for each sub-dose field of the plurality of sub-dose fields, determining a deformation field by performing an image registration operation on the group of sub-verification images corresponding to the sub-dose field and a preset image. The method may include determining a deformation sub-dose field based on the sub-dose field and the deformation field. The method may include determining the target dose field by combining a plurality of deformation sub-dose fields corresponding to the plurality of sub-dose fields.

In some embodiments, the preset image may include a plan image or a sub-verification image of a plurality of groups of sub-verification images corresponding to the plurality of groups of sub-target images.

In some embodiments, the method may include determining a dose verification result by comparing the target dose field and a plan dose field.

According to another aspect of the present disclosure, a radiation system may include at least one storage medium including a set of instructions, and at least one processor in communication with the at least one storage medium. When executing the set of instructions, the at least one processor may be directed to cause the system to perform a method. The method may include obtaining a target image of the subject acquired during the radiation operation and corresponding target physiological motion information of the subject. The method may include dividing the target image into a plurality of groups of sub-target images based on the target physiological motion information. The plurality of groups of sub-target images may correspond to a plurality of phases of the target physiological motion information. The method may include, for each group of the plurality of groups of sub-target images, obtaining a group of sub-verification images corresponding to the group of sub-target images. The group of sub-verification images and the group of sub-target images may correspond to a same phase. The method may include determining a sub-dose field based on the group of sub-target images and the group of sub-verification images. The method may include determining a target dose field corresponding to the target image based on a plurality of sub-dose fields corresponding to the plurality of groups of sub-target images.

In some embodiments, the method may include obtaining a plurality of reference images of the subject and corresponding reference physiological motion information of the subject. The method may include establishing a correlation model based on the plurality of reference images and the reference physiological motion information. The method may include obtaining the group of sub-verification images corresponding to the group of sub-target images based on the correlation model.

In some embodiments, the correlation model may reflect a relationship between the plurality of reference images and phases of the reference physiological motion information respectively. The method may include determining one or more reference images corresponding to a phase corresponding to the group of sub-target images based on the correlation model as the group of sub-verification images corresponding to the group of sub-target images.

According to another aspect of the present disclosure, a radiation method may be implemented on a computing device including at least one processor and at least one storage device. The method may include obtaining a plurality of reference images of a target of a subject and reference physiological motion information of the subject. The plurality of reference images and the reference physiological motion information may be acquired in a radiation period. The method may include establishing a correlation model based on the plurality of reference images and the reference physiological motion information. The method may include monitoring real-time motion information of the target based on the correlation model during a radiation operation performed during the radiation period.

In some embodiments, the method may include obtaining a positioning reference image of the subject. The method may include obtaining a plurality of candidate images of the target of the subject. The method may include determining the plurality of reference images of the target by combining the plurality of candidate images of the target and the positioning reference image of the subject.

In some embodiments, the reference physiological motion information may include a respiratory signal or an image feature related to a respiratory motion of the subject.

In some embodiments, the correlation model may reflect a relationship between the plurality of reference images and phases of the reference physiological motion information respectively.

In some embodiments, the method may include obtaining a target image of the subject acquired during the radiation operation and corresponding target physiological motion information of the subject. The method may include determining a target phase based on the target physiological motion information. The method may include obtaining a target reference image based on the target phase and the correlation model. The method may include monitoring the real-time motion information of the target by comparing the target reference image and the target image.

In some embodiments, the method may include adjusting at least one parameter associated with the radiation operation based on the real-time motion information of the target.

In some embodiments, the method may include obtaining a target image of the subject acquired during the radiation operation and corresponding target physiological motion information of the subject. The method may include dividing the target image into a plurality of groups of sub-target images based on the target physiological motion information. The plurality of groups of sub-target images may correspond to a plurality of phases of the target physiological motion information. The method may include, for each group of the plurality of groups of sub-target images, obtaining a group of sub-verification images corresponding to the group of sub-target images. The group of sub-verification images and the group of sub-target images may correspond to a same phase. The method may include determining a sub-dose field based on the group of sub-target images and the group of sub-verification images. The method may include determining a target dose field corresponding to the target image based on a plurality of sub-dose fields corresponding to the plurality of groups of sub-target images.

According to another aspect of the present disclosure, a non-transitory computer readable medium may include at least one set of instructions. When executed by at least one processor of a computing device, the at least one set of instructions may cause the at least one processor to effectuate a method. The method may include obtaining a plurality of reference images of a target of a subject and reference physiological motion information of the subject. The plurality of reference images and the reference physiological motion information may be acquired in a radiation period. The method may include establishing a correlation model based on the plurality of reference images and the reference physiological motion information. The method may include monitoring real-time motion information of the target based on the correlation model during a radiation operation performed during the radiation period.

According to another aspect of the present disclosure, a non-transitory computer readable medium may include at least one set of instructions. When executed by at least one processor of a computing device, the at least one set of instructions may cause the at least one processor to effectuate a method. The method may include obtaining a target image of the subject acquired during the radiation operation and corresponding target physiological motion information of the subject. The method may include dividing the target image into a plurality of groups of sub-target images based on the target physiological motion information. The plurality of groups of sub-target images may correspond to a plurality of phases of the target physiological motion information. The method may include, for each group of the plurality of groups of sub-target images, obtaining a group of sub-verification images corresponding to the group of sub-target images. The group of sub-verification images and the group of sub-target images may correspond to a same phase. The method may include determining a sub-dose field based on the group of sub-target images and the group of sub-verification images. The method may include determining a target dose field corresponding to the target image based on a plurality of sub-dose fields corresponding to the plurality of groups of sub-target images.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings.

The drawings are not to scale. These embodiments are non-limiting exemplary embodiments, in which like reference numerals represent similar structures throughout the several views of the drawings, and wherein:

FIG. 4 is a flowchart illustrating an exemplary process for monitoring real-time motion information of a target of a subject according to some embodiments of the present disclosure;

DETAILED DESCRIPTION

Figure 1:
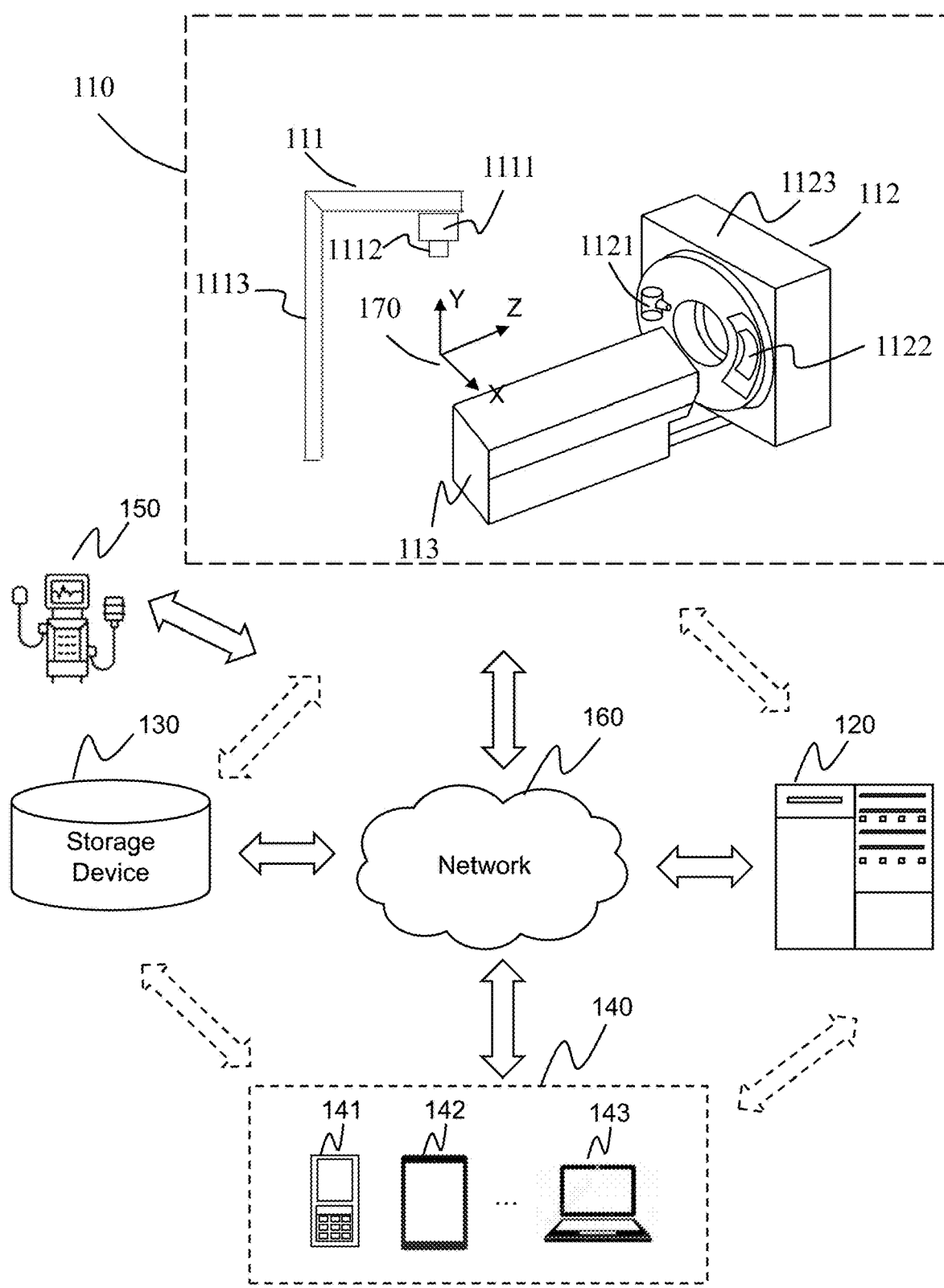
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different level in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

An aspect of the present disclosure relates to systems and methods for radiation therapy. A processing device may obtain a plurality of reference images of a target of a subject and reference physiological motion information of the subject. The plurality of reference images and the reference physiological motion information may be acquired in a radiation period. The processing device may establish a correlation model based on the plurality of reference images and the reference physiological motion information. The processing device may monitor real-time motion information of the target based on the correlation model during a radiation operation performed during the radiation period.

According to some embodiments of the present disclosure, the real-time motion information of the target may be monitored based on the correlation model during the radiation operation performed during the radiation period. That is, the correlation model may be established based on data and/or information (e.g., the plurality of reference images, the reference physiological motion information) that is acquired shortly before the radiation operation (e.g., several minutes or hours before the radiation operation), accordingly, the correlation model can (substantially) reflect a relationship between feature information of the target of the subject and phases of a physiological motion of the subject during the radiation operation. In addition, since the acquisition of the plurality of reference images and the reference physiological motion information and the real-time monitoring of the subject are located at a same radiation period, position information of the subject (e.g., a relative position between the subject and a scanning table) during the acquisition of the plurality of reference images and the reference physiological motion information is (substantially) the same as position information of the subject during the radiation operation, which can also improve the monitoring accuracy of the motion information of the target.

In some embodiments, the processing device may obtain a target image of the subject acquired during the radiation operation and corresponding target physiological motion information of the subject. The processing device may divide the target image into a plurality of groups of sub-target images based on the target physiological motion information. The plurality of groups of sub-target images may correspond to a plurality of phases of the target physiological motion information. For each group of the plurality of groups of sub-target images, the processing device may obtain a sub-verification image (or a group of sub-verification images) corresponding to the group of sub-target images. The sub-verification image (or the group of sub-verification images) and the group of sub-target images may correspond to a same phase. The sub-verification image (or the group of sub-verification images) corresponding to the group of sub-target images may be obtained by dividing a verification image. The processing device may determine a sub-dose field based on the group of sub-target images and the sub-verification image (or the group of sub-verification images). The processing device may determine a target dose field corresponding to the target image based on a plurality of sub-dose fields corresponding to the plurality of groups of sub-target images.

According to some embodiments of the present disclosure, the target image and the verification image may both include time information, and the target image and the verification image may be divided based on the time information of the target image, the time information of the verification image, and corresponding target physiological motion information of the subject. Accordingly, the radiation dose verification methods and systems disclosed herein can improve the accuracy of the radiation dose verification, and facilitate the determination of radiation plan of the subject.

FIG. 1 is a schematic diagram illustrating an exemplary medical system according to some embodiments of the present disclosure. The medical system 100 may include a medical device 110, a processing device 120, a storage device 130, a terminal device 140, a network 160, and a detection device 150. In some embodiments, two or more components of the medical system 100 may be connected to and/or communicate with each other via a wireless connection (e.g., the network 160), a wired connection, or a combination thereof. The connection between the components of the medical system 100 may be variable. Merely by way of example, the medical device 110 may be connected to the processing device 120 through the network 160 or directly as indicated by the bi-directional arrow in dotted lines linking the medical device 110 and the processing device 120. As another example, the storage device 130 may be connected to the medical device 110 through the network 160 or directly as indicated by the bi-directional arrow in dotted lines linking the storage device 130 and the medical device 110. As still another example, the terminal device 140 may be connected to the processing device 120 through the network 160 or directly as indicated by the bi-directional arrow in dotted lines linking the terminal device 140 and the processing device 120. As still another example, the terminal device 140 may be connected to the storage device 130 through the network 160 or directly as indicated by the bi-directional arrow in dotted lines linking the terminal device 140 and the storage device 130.

In some embodiments, the medical device 110 may be an RT device. The RT device may be configured to deliver a radiation therapy treatment. For example, the RT device may deliver one or more radiation beams to a target (e.g., a tumor) of a subject (e.g., a patient) for causing an alleviation of the subject's disease and/or symptoms. In some embodiments, the RT device may be a conformal radiation therapy device, an image guided radiation therapy (IGRT) device, an intensity modulated radiation therapy (IMRT) device, an intensity modulated arc therapy (IMAT) device, etc.

In some embodiments, as illustrated in FIG. 1, the medical device 110 may include a treatment device 111, an imaging device 112, and a scanning table 113.

The treatment device 111 may be configured to perform a radiation operation on the subject. The subject may include any biological subject (e.g., a human being, an animal, a plant, or a portion thereof) and/or a non-biological subject (e.g., a phantom, structure/device to be non-destructively tested). In some embodiments, the treatment device 111 may include a treatment radiation source 1111, a collimator 1112, and a gantry 1113. The treatment radiation source 1111 may be configured to generate and emit a radiation beam (e.g., electrons, photons) toward the subject for treatment. The collimator 1112 may be configured to control the shape of the radiation beam generated by the treatment radiation source 1111. The gantry 1113 may be configured to support the treatment radiation source 1111 and the collimator 1112. In some embodiments, the treatment radiation source 1111 may include a linear accelerator (LINAC) configured to accelerate electrons, ions, or protons. In some embodiments, the treatment radiation source 1111 may include a gamma knife, a cyber knife, a proton and heavy ion device, etc.

The imaging device 112 may be configured to perform an imaging operation prior to the radiation operation, during the radiation operation, and/or after the radiation operation. In some embodiments, the imaging device 112 may include an X-ray imaging device, a computed tomography (CT) device (e.g., a 3D CT device, a 4D CT device), or the like, or any combination thereof. In some embodiments, the imaging device 112 may include a cone beam computed tomography (CBCT) device, a multislice computed tomography (MSCT) device, a fan-beam computed tomography (FBCT) device, or the like, or any combination thereof. In some embodiments, the imaging device 112 may include an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof.

In some embodiments, the imaging device 112 may include an imaging radiation source 1121, a detector 1122, and a gantry 1123. The imaging radiation source 1121 and the detector 1122 may be mounted on the gantry 1123. The imaging radiation source 1121 may emit radioactive rays to the subject. The detector 1122 may detect radiation events (e.g., X-ray photons, gamma-ray photons) emitted from an imaging region of the imaging device 112. In some embodiments, the detector 1122 may include one or more detector units. The detector unit(s) may include a scintillationdetector (e.g., a cesium iodide detector, a gadolinium oxysulfide detector), a gas detector, etc. The detector unit(s) may include a single-row detector and/or a multi-row detector.

The scanning table 113 may be configured to support the subject to be treated and/or imaged. In some embodiments, the scanning table 113 may be movable between the treatment device 111 and the imaging device 112 along a Z-axis direction of a coordinate system 170 shown in FIG. 1.

Figure 7A:
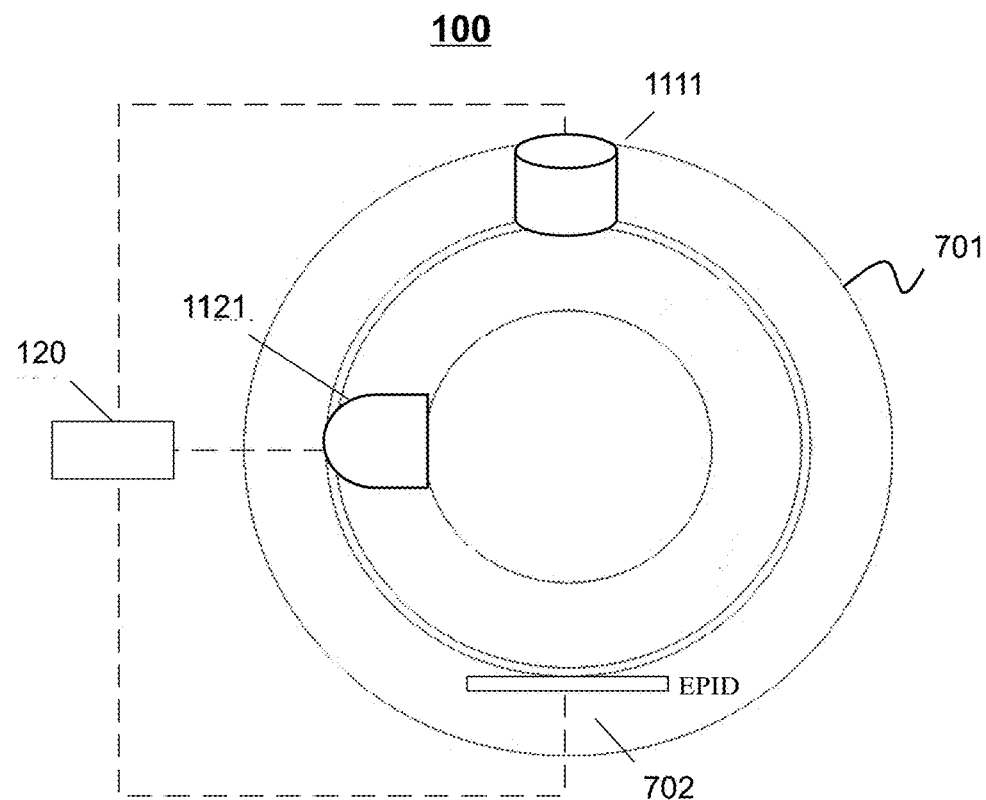
FIG. 7A is a schematic diagram illustrating an exemplary medical system according to some embodiments of the present disclosure.
Figure 7B:
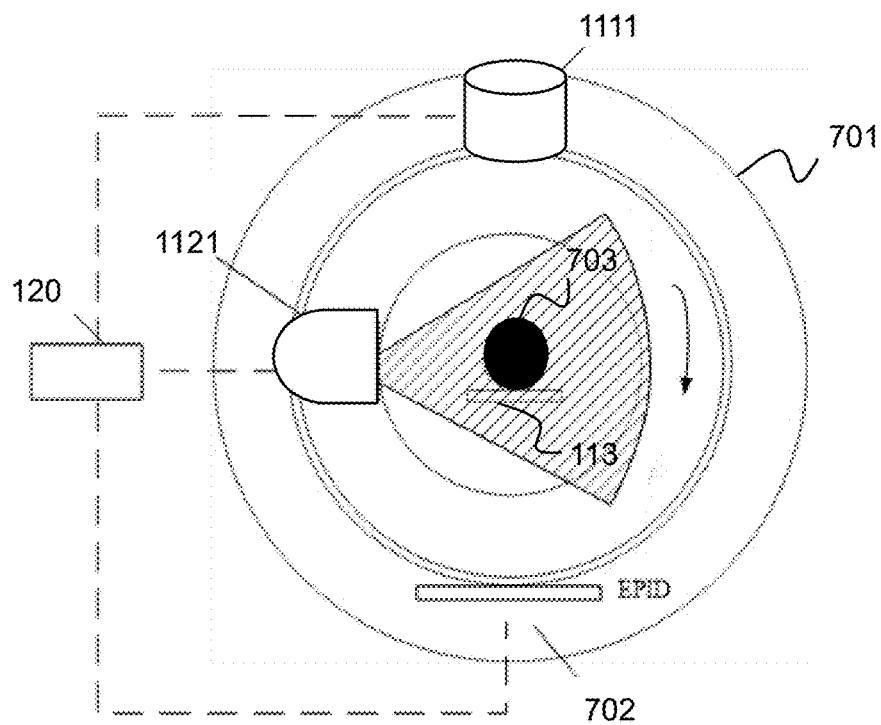
FIG. 7B is a schematic diagram illustrating an exemplary medical system according to some embodiments of the present disclosure.

In some embodiments, as illustrated in FIG. 7B, the treatment radiation source 1111 and/or the imaging radiation source 1121 may rotate around a rotation axis to be positioned at various gantry angles, such that the subject (e.g., a subject 703) located in the scanning table 113 may be imaged and/or treated from a plurality of directions. Merely by way of example, the treatment radiation source 1111 may be fixedly attached to the gantry 1113, and a detector may be fixedly or flexibly attached to the gantry 1113 opposite to the treatment radiation source 1111. When the gantry 1113 rotates around a gantry rotation axis in a circular path, the treatment radiation source 1111 and the detector attached on the gantry 1113 may rotate along with the gantry 1113, and the subject located in the scanning table 113 may be imaged and/or treated from a plurality of gantry angles. As used herein, a gantry angle relates to a position of a radiation source (e.g., the treatment radiation source 1111) with reference to a medical device (e.g., the treatment device 111). For example, a gantry angle may be an angle between a vertical direction (e.g., a Y axis direction of the coordinate system 170 shown in FIG. 1) and a direction of a beam axis of a radiation beam emitted from the treatment radiation source 1111 of the treatment device 111.

In some embodiments, the imaging device 112 may be spaced by a distance from the treatment device 111. In some embodiments, the gantry 1123 of the imaging device 112 and the gantry 1113 of the treatment device 111 may share an axis of rotation. In some embodiments, the imaging radiation source 1121 and the treatment radiation source 1111 may be integrated as one radiation source to image and/or treat the subject. In some embodiments, the imaging device 112 and the treatment device 111 may share a same gantry. For example, as illustrated in FIG. 7A and FIG. 7B, the medical device 110 may include an electronic portal imaging device (EPID) 702, the treatment radiation source 1111 and the imaging radiation source 1121 may be mounted on a gantry 701. The gantry 701 may be a O-shaped gantry, a L-shaped gantry, a C-shaped gantry, etc. In some embodiments, a treatment beam emitted from the treatment radiation source 1111 and an imaging beam emitted from the imaging radiation source 1121 may be coplanar or non-coplanar.

In some embodiments, the treatment device 111 may correspond to a treatment isocenter. For example, the treatment isocenter of the treatment device 111 may be a rotation center of the treatment radiation source 1111 during the radiation operation. In some embodiments, the imaging device 112 may correspond to an imaging isocenter. For example, the imaging isocenter of the imaging device 112 may be a rotation center of the imaging radiation source 1121 during the imaging operation. In some embodiments, the treatment isocenter may be aligned with the imaging isocenter. Accordingly, there is no need to move the subject from an imaging position (or region) to a treatment position (or region) and position errors can be avoided. In some embodiments, the treatment isocenter may be considered to be aligned with the imaging isocenter if a distance between the imaging isocenter and the imaging isocenter is less than a distance threshold. The distance threshold may be manually set by a user of the medical system 100, or determined by one or more components of the medical system 100 according to different situations.

In some embodiments, the medical device 110 may include an imaging mode (e.g., a CT mode) and a radiation mode. In the imaging mode, the imaging device 112 may acquire an image of the subject. For example, a series of 3D images of the subject corresponding to different time points (or time periods) may be obtained by performing a four-dimensional computed tomography (4DCT) imaging on the subject. In the radiation mode, the treatment device 111 may deliver one or more radiation beams to a target (e.g., a tumor) of the subject according to a radiation plan. In some embodiments, the imaging device 112 may acquire an image of the subject during the radiation operation, to realize a real-time imaging of the subject during the radiation operation. In some embodiments, a scan range of the image acquired by the imaging device 112 may need to cover a moving range of the target of the subject during the radiation operation.

The processing device 120 may process information obtained from the medical device 110, the terminal device 140, and/or the storage device 130. For example, the processing device 120 may obtain a plurality of reference images of a target of a subject and reference physiological motion information of the subject. Then the processing device 120 may establish a correlation model based on the plurality of reference images and the reference physiological motion information. Further, the processing device 120 may monitor real-time motion information of the target based on the correlation model during a radiation operation performed during a radiation period. As another example, the processing device 120 may obtain a target image of a subject acquired during a radiation operation and corresponding target physiological motion information of the subject. Then the processing device 120 may divide the target image into a plurality of groups of sub-target images based on the target physiological motion information. Further, for each group of a plurality of groups of sub-target images, the processing device 120 may obtain a sub-verification image corresponding to the group of sub-target images. Furthermore, for each group of a plurality of groups of sub-target images, the processing device 120 may determine a sub-dose field based on the group of sub-target images and a sub-verification image. Then the processing device 120 may determine a target dose field corresponding to a target image based on a plurality of sub-dose fields corresponding to a plurality of groups of sub-target images.

Figure 2:
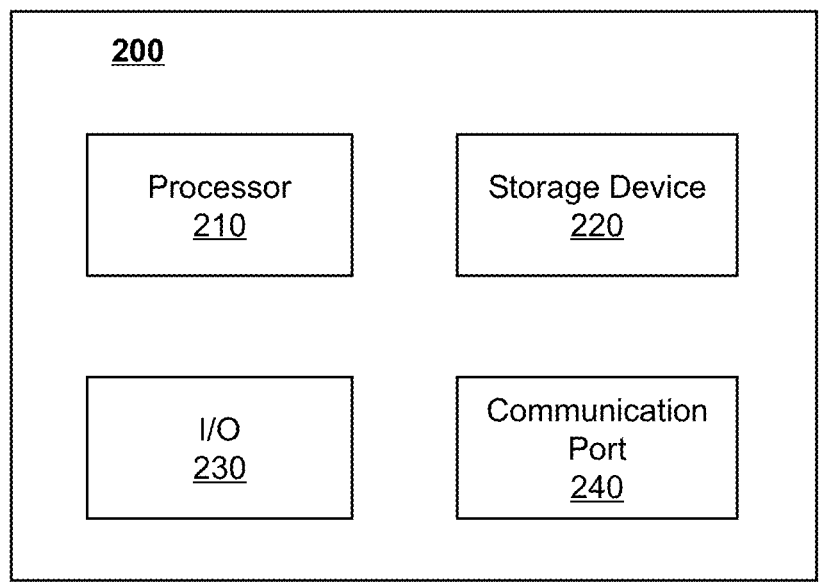
FIG. 2 is a schematic diagram illustrating exemplary hardware and/or software components of an exemplary computing device according to some embodiments of the present disclosure.

In some embodiments, the processing device 120 may be a computer, a user console, a single server, a server group, etc. The server group may be centralized or distributed. In some embodiments, the processing device 120 may be local or remote. For example, the processing device 120 may access information stored in the medical device 110, the terminal device 140, and/or the storage device 130 via the network 160. As another example, the processing device 120 may be directly connected to the medical device 110, the terminal device 140, and/or the storage device 130 to access stored information. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device 200 having one or more components as illustrated in FIG. 2.

The storage device 130 may store data, instructions, and/or any other information. In some embodiments, the storage device 130 may store data obtained from the terminal device 140 and/or the processing device 120. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 160 to communicate with one or more other components (e.g., the processing device 120, the terminal device 140) of the medical system 100. One or more components of the medical system 100 may access the data and/or instructions stored in the storage device 130 via the network 160. In some embodiments, the storage device 130 may be directly connected to or communicate with one or more other components (e.g., the processing device 120, the terminal device 140) of the medical system 100. In some embodiments, the storage device 130 may be part of the processing device 120. In some embodiments, the storage device 130 may be connected to or communicate with the medical device 110 via the network 160, or at the backend of the processing device 120.

The terminal device 140 may enable user interaction between a user and the medical system 100. In some embodiments, the terminal device 140 may include a mobile device 141, a tablet computer 142, a laptop computer 143, or the like, or any combination thereof. In some embodiments, the mobile device 141 may include a smart home device, a wearable device, a mobile device, a virtual reality device, an augmented reality device, or the like, or any combination thereof. In some embodiments, the terminal device 140 may be part of the processing device 120.

The detection device 150 may be configured to obtain physiological motion information of a subject prior to the radiation operation, during the radiation operation, and/or after the radiation operation. For example, the detection device 150 may obtain reference physiological motion information of the subject before a radiation operation performed during a radiation period. As another example, the detection device 150 may obtain target physiological motion information of the subject during the radiation operation.

The physiological motion information may reflect motion information of a tissue or an organ that is caused or influenced by a physiological motion of the subject. In some embodiments, the physiological motion information may include respiratory motion information, cardiac motion information, or the like, or any combination thereof. More descriptions of the physiological motion information may be found elsewhere in the present disclosure (e.g., FIG. 4 and descriptions thereof).

In some embodiments, the detection device 150 may include a non-contact detection device and/or a contact detection device. In some embodiments, a non-contact detection device indicates that the detection device does not need to be in contact with a subject when detecting physiological motion information or that the detection of the physiological motion information of the subject by the detection device does not depend on the detection device being in contact with the subject. For example, the detection device 150 may include an optical surface monitoring device, a radar sensor, a sensor-based mattress, an infrared camera, or the like, or any combination thereof. In some embodiments, a contact detection device indicates that the detection device needs to be in contact with a subject for detecting physiological motion information of the subject. For example, the contact detection device may include an electrocardiographic device (e.g., an electrocardiograph), a pulse measuring device, a carbon dioxide sensor, a respiratory flow meter, a respiratory belt, a pressure measurement device to measure the change of pressure during the respiratory motion of the subject, or the like, or any combination thereof.

In some embodiments, the detection device 150 may acquire the physiological motion information (e.g., the respiratory motion information) by various motion information acquisition methods. The motion information acquisition methods may include a real-time image-based feature recognition technology, an optical surface imaging technology, an infrared marking technology, a respiratory belt technology, or the like, or any combination thereof.

In some embodiments, the detection device 150 may process the physiological motion information of the subject. For example, after a physiological motion signal (e.g., a respiratory signal) is acquired by the detection device 150, the detection device 150 may perform a filtering operation, a noise reduction operation, a smoothing operation, or the like, on the physiological motion signal.

The network 160 may include any suitable network that can facilitate the exchange of information and/or data for the medical system 100. In some embodiments, one or more components (e.g., the medical device 110, the terminal device 140, the processing device 120, the storage device 130) of the medical system 100 may communicate information and/or data with one or more other components of the medical system 100 via the network 160. For example, the processing device 120 may obtain an image (e.g., a reference image, a target image) of a target of a subject from the medical device 110 via the network 160. As another example, the processing device 120 may obtain physiological motion information (e.g., reference physiological motion information, target physiological motion information) of a subject from the detection device 150 via the network 160.

In some embodiments, the network 160 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. In some embodiments, the network 160 may include one or more network access points. For example, the network 160 may include wired and/or wireless network access points such as base stations and/or internet exchange points through which one or more components of the medical system 100 may be connected to the network 160 to exchange data and/or information.

In some embodiments, a coordinate system may be provided for the medical system 100 to define a position of a component (e.g., an absolute position, a position relative to another component) and/or a movement of the component. For illustration purposes, the coordinate system 170 may include the X-axis, the Y-axis, and the Z-axis. The X-axis and the Z-axis shown in FIG. 1 may be horizontal, and the Y-axis may be vertical. As illustrated, a positive X direction along the X-axis may be from the left side to the right side of the scanning table 113 viewed from the direction facing the front of the medical device 110; a positive Y direction along the Y-axis may be from the lower part (or from the floor where the medical system 100 stands) to the upper part of the gantry 1123; and a positive Z direction along the Z-axis may be the direction in which the scanning table 113 is moved from the outside into the medical system 100 viewed from the direction facing the front of the medical device 110.

It should be noted that the above description regarding the medical system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical system 100 may include one or more additional components and/or one or more components of the medical system 100 described above may be omitted. For example, the detection device 150 may be omitted. In some embodiments, two or more components of the medical system 100 may be integrated into a single component. A component of the medical system 100 may be implemented on two or more sub-components. For example, the detection device 150, the storage device 130, the terminal device 140, and/or the processing device 120 may be part of the medical device 110.

FIG. 2 is a schematic diagram illustrating exemplary hardware and/or software components of an exemplary computing device according to some embodiments of the present disclosure. The computing device 200 may be used to implement any component of the medical system 100 as described herein. For example, the processing device 120 and/or the terminal device 140 may be implemented on the computing device 200, respectively, via its hardware, software program, firmware, or a combination thereof. Although only one such computing device is shown, for convenience, the computer functions relating to the medical system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data obtained from the medical device 110, the terminal device 140, the storage device 130, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the medical system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input and/or output signals, data, information, etc. In some embodiments, the I/O 230 may enable user interaction with the processing device 120. In some embodiments, the I/O 230 may include an input device and an output device. The input device may include alphanumeric and other keys that may be input via a keyboard, a touch screen (e.g., with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 160) to facilitate data communications. The communication port 240 may establish connections between the processing device 120 and the medical device 110, the terminal device 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3A:
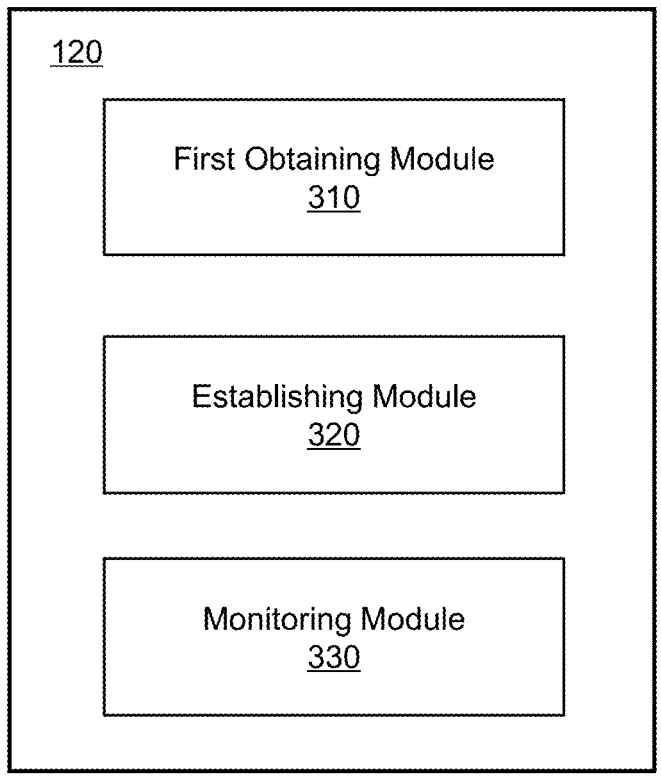
FIG. 3A is a block diagram illustrating an exemplary processing device according to some embodiments of the present disclosure.

FIG. 3A is a block diagram illustrating an exemplary processing device according to some embodiments of the present disclosure. In some embodiments, the processing device 120 may include a first obtaining module 310, an establishing module 320, and a monitoring module 330.

The first obtaining module 310 may be configured to obtain data and/or information associated with motion monitoring. The data and/or information associated with motion monitoring may include a reference image, a positioning reference image, a candidate image, reference physiological motion information, or the like, or any combination thereof. In some embodiments, the first obtaining module 310 may obtain a plurality of reference images of a target of a subject. For example, the first obtaining module 310 may obtain a positioning reference image of a subject. The first obtaining module 310 may obtain a plurality of candidate images of a target of the subject. The first obtaining module 310 may determine a plurality of reference images of the target by combining the plurality of candidate images of the target and the positioning reference image of the subject. In some embodiments, the first obtaining module 310 may obtain reference physiological motion information of the subject. More descriptions for obtaining the plurality of reference images and the reference physiological motion information may be found elsewhere in the present disclosure (e.g., operation 510 in FIG. 5, FIG. 6, and descriptions thereof).

The establishing module 320 may be configured to establish a correlation model. In some embodiments, the establishing module 320 establish a correlation model based on time information of a plurality of reference images and time information of reference physiological motion information. For example, the establishing module 320 may establish a correlation model by correlating reference image(s) with reference physiological motion information that are acquired at a same time point (or during a same time period). More descriptions of the correlation model may be found elsewhere in the present disclosure (e.g., operation 520 in FIG. 5, and descriptions thereof).

The monitoring module 330 may be configured to monitor real-time motion information of a target of a subject based on a correlation model during a radiation operation performed during a radiation period. In some embodiments, the monitoring module 330 may obtain a target image of the subject acquired during the radiation operation and corresponding target physiological motion information of the subject. The monitoring module 330 may determine a target phase based on the target physiological motion information. The monitoring module 330 may obtain a target reference image based on the target phase and a correlation model. Then the monitoring module 330 may monitor the real-time motion information of the target by comparing the target reference image and the target image. More descriptions for monitoring the real-time motion information of the target may be found elsewhere in the present disclosure (e.g., operation 530 in FIG. 5, FIG. 6, and descriptions thereof).

Figure 3B:
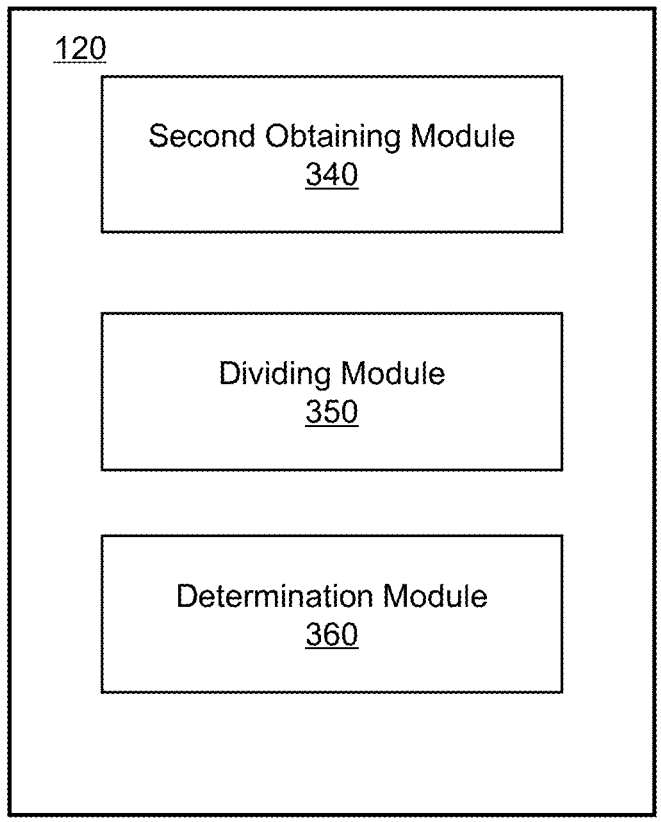
FIG. 3B is a block diagram illustrating an exemplary processing device according to some embodiments of the present disclosure.

FIG. 3B is a block diagram illustrating an exemplary processing device according to some embodiments of the present disclosure. In some embodiments, the processing device 120 may include a second obtaining module 340, a dividing module 350, and a determination module 360.

The second obtaining module 340 may be configured to obtain data and/or information associated with radiation dose verification. The data and/or information associated with radiation dose verification may include a target image, target physiological motion information, a verification image, a sub-verification image, or the like, or any combination thereof. In some embodiments, the second obtaining module 340 may obtain a target image of a subject acquired during a radiation operation and corresponding target physiological motion information of the subject. More descriptions for obtaining the target image and the target physiological motion information of the subject may be found elsewhere in the present disclosure (e.g., operation 910 in FIG. 9, and descriptions thereof). In some embodiments, the second obtaining module 340 may obtain a verification image or a sub-verification image. More descriptions of the verification image or a sub-verification image may be found elsewhere in the present disclosure (e.g., operation 930 in FIG. 9, and descriptions thereof).

The dividing module 350 may be configured to divide an image. In some embodiments, the dividing module 350 may divide the target image into a plurality of groups of sub-target images based on target physiological motion information. For example, the dividing module 350 may generate a processed target image by processing a target image based on time information of the target image and time information of target physiological motion information. The dividing module 350 may divide at least part of the target physiological motion information into a plurality of phases based on a cycle of the target physiological motion information. The dividing module 350 may divide the processed target image into the plurality of groups of sub-target images based on the plurality of phases. In some embodiments, the dividing module 350 may divide a verification image into a plurality of sub-verification images (or a plurality of groups of sub-verification images) based on candidate physiological motion information. More descriptions for dividing the target image and the verification image may be found elsewhere in the present disclosure (e.g., operation 920 and 930 in FIG. 9, FIG. 10, FIG. 11, and descriptions thereof).

The determination module 360 may be configured to determine a dose field. In some embodiments, the determination module 360 may determine a sub-dose field based on a group of sub-target images and a corresponding sub-verification image (or a corresponding group of sub-verification images). The determination module 360 may determine a target dose field corresponding to a target image based on a plurality of sub-dose fields corresponding to a plurality of groups of sub-target images. More descriptions for determining the sub-dose field and the target dose field may be found elsewhere in the present disclosure (e.g., operation 940 and 950 in FIG. 9, FIGS. 12-14, and descriptions thereof).

It should be noted that the above descriptions of the processing device 120 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. In some embodiments, the processing device 120 may include one or more other modules and/or one or more modules described above may be omitted. For example, establishing module 320 may be omitted. Additionally or alternatively, two or more modules may be integrated into a single module and/or a module may be divided into two or more units. For example, the first obtaining module 310 and the second obtaining module 340 may be integrated into a single module.

FIG. 4 is a flowchart illustrating an exemplary process for monitoring real-time motion information of a target of a subject according to some embodiments of the present disclosure. In some embodiments, process 400 may be executed by the medical system 100. For example, the process 400 may be implemented as a set of instructions (e.g., an application) stored in a storage device (e.g., the storage device 130, the storage 220). In some embodiments, the processing device 120 (e.g., the processor 210 of the computing device 200, and/or one or more modules illustrated in FIG. 3) may execute the set of instructions and may accordingly be directed to perform the process 400.

In 410, the processing device 120 (e.g., the first obtaining module 310) may obtain a plurality of reference images of a target of a subject and reference physiological motion information of the subject.

In some embodiments, the target of the subject may be a region (e.g., a tumor) of the subject (e.g., a patient) that needs to be imaged and/or treated. In some embodiments, the target may be a region of the subject that may be influenced by a physiological motion of the subject. For example, the target may include the chest, the abdomen, the heart, a lung, a liver, or the like, or any combination thereof.

In some embodiments, the reference image may include a CT image, an MRI image, a PET image, a PET-CT image, an MRI-CT image, etc. In some embodiments, the reference image may be a two-dimensional (2D) image, a three-dimensional (3D) image, a four-dimensional (4D) image, etc. For example, the plurality of reference images may be 4D CT images that are acquired by performing a cine 4D-CT scan on the subject. In some embodiments, the medical device 110 may obtain a plurality of sets of scan data (e.g., CT scan data) by performing a scan (e.g., a CT scan) on the target of the subject. Then the processing device 120 may generate the plurality of reference images based on the plurality of sets of scan data according to a reconstruction algorithm (e.g., a filter back projection (FBP) algorithm, a back-projection filter (BFP) algorithm).

In some embodiments, the plurality of reference images may include time information. For example, the plurality of reference images may be a series of 3D images or 2D images corresponding to different time points (or time periods). As used herein, "an image corresponds to a specific time point (or a specific time period)" refers to that the image is generated based on scan data that is acquired at the specific time point (or during the specific time period).

In some embodiments, the processing device 120 may obtain the plurality of reference images from one or more components (e.g., the medical device 110, the terminal 140, the storage device 130) of the medical system 100 or an external storage device via the network 160. For example, the medical device 110 may transmit the plurality of reference images to the storage device 130 or any other storage device for storage. The processing device 120 may obtain the plurality of reference images from the storage device 130 or any other storage device. As another example, the processing device 120 may obtain the plurality of reference images from the medical device 110 directly. In some embodiments, the processing device 120 may determine the plurality of reference images by combining a plurality of candidate images of the target and a positioning reference image of the subject. More descriptions for determining the plurality of reference images may be found elsewhere in the present disclosure (e.g., FIG. 5 and descriptions thereof).

In some embodiments, the reference physiological motion information may include respiratory motion information, cardiac motion information, etc. In some embodiments, the reference physiological motion information may include a reference physiological motion signal (e.g., a reference respiratory signal, a reference cardiac signal) that may be acquired by a detection device (e.g., the detection device 150).

In some embodiments, take the "reference respiratory signal" as an example, the reference respiratory signal may indicate a respiratory cycle of the subject, a respiratory amplitude, a respiratory frequency, or the like, or a combination thereof. In some embodiments, the respiratory cycle may include a plurality of respiratory phases reflecting a plurality of respiratory stages in a respiratory motion of the subject. Each respiratory phase may correspond to a time point (or a time period) in the respiratory cycle. In some embodiments, the respiratory phases of the subject (e.g., a patient) may include an intermediate inspiration phase, an end-inspiration phase, an intermediate expiration phase, an end-expiration phase, or the like, or any combination thereof. The intermediate inspiration phase and the end-inspiration phase may also be referred to as an inspiration phase; the intermediate expiration phase and the end-expiration phase may also be referred to as an expiration phase. For example, in the inspiration phase, the patient may expand his/her chest to cause a negative pressure in the chest, wherein the negative pressure may cause the air to flow into the lungs of the patient; in the expiration phase, the patient may shrink the chest to cause a positive pressure in the chest, wherein the positive pressure may push the air out of the lungs.

In some embodiments, the reference respiratory signal may be represented in a form a respiratory motion curve (e.g., a sine curve, a cosine curve). The respiratory motion curve may reflect the change of respiratory amplitude of the subject over time. For example, as illustrated in FIGS. 11(A)-(D), the abscissa of the respiratory motion curve may be "time" and the ordinate of the respiratory motion curve may be "respiratory amplitude." In some embodiments, a peak of the respiratory motion curve may correspond to an end of an expiration process, and a valley of the respiratory motion curve may correspond to an end of an inspiration process. Alternatively, the peak of the respiratory motion curve may correspond to the end of the inspiration process, and the valley of the respiratory motion curve may correspond to the end of the expiration process.

In some embodiments, the reference physiological motion information may include a reference image feature related to the physiological motion of the subject. In some embodiments, the reference image feature related to the physiological motion of the subject may reflect feature information (e.g., a contour) of the subject and/or feature information (e.g., a size, a contour, a position) of a region (e.g., an organ, tissue) that may be influenced by the physiological motion of the subject. For example, the reference physiological motion information may include a reference image feature of a diaphragm that is related to respiratory motion of the subject. In some embodiments, the processing device 120 may determine the reference image feature related to the physiological motion of the subject based on the plurality of reference images according to an image analysis algorithm (e.g., an image segmentation algorithm, a feature point extraction algorithm).

In some embodiments, the reference physiological motion information may include time information. For example, the time information may include a time point (or a time period) at which the reference physiological motion signal is acquired by the detection device 150. As another example, the time information may include a time point (or a time period) at which an image (that is used to determine the reference image feature related to the physiological motion of the subject) is acquired by a medical device.

In some embodiments, the plurality of reference images and the reference physiological motion information may be acquired in a radiation period. The radiation period may be a time period during a single radiation therapy treatment process (also referred to as a course of a radiotherapy session) of the subject. In some embodiments, in a fractionated radiation therapy, a single radiation therapy treatment process may refer to a fraction of the fractionated radiation therapy.

In some embodiments, before the single radiation therapy treatment process, a plan image of the subject may be obtained to determine a radiation plan. In some embodiments, the plan image may show the target and one or more tissues or organs nearby the target of the subject. In some embodiments, the plan image may include a CT image, an MRI image, a PET image, a PET-CT image, an SPECT-MRI image, etc. In some embodiments, the plan image may include a 2D image, a 3D image, etc. In some embodiments, the radiation plan may describe how a radiation therapy treatment is performed on the subject. For example, the radiation plan may include value(s) or value range(s) of at least one scanning parameter (e.g., a radiation dose rate, a radiation duration, a gantry angle, a gantry movement speed, a gantry movement acceleration, a collimator angle, a collimator rotation speed), a planned total dosage and/or a planned dose distribution of the subject, or the like, or any combination thereof.

In some embodiments, when the single radiation therapy treatment process is to be executed, the subject may be positioned in an imaging region of the imaging device 112 and a positioning reference image of the subject may be obtained. Then the plan image and the positioning reference image may be registered to generate a registration result. Further, a target positioning may be performed on the subject based on the registration result. For example, a position of the scanning table that supports the subject may be adjusted based on the registration result, such that the target of the subject is positioned at the treatment isocenter of the treatment device 111. Furthermore, a radiation operation may be performed on the subject.

In some embodiments, the radiation period of the single radiation therapy treatment process may refer to a time period between the target positioning of the subject and the radiation operation of the subject. For example, the radiation period may be a time period from a start time of the target positioning of the subject to an end time (or a start time) of the radiation operation of the subject. As another example, the radiation period may be a time period from an end time of the target positioning of the subject to the start time (or the end time) of the radiation operation of the subject.

In some embodiments, the plurality of reference images and the reference physiological motion information may be acquired during a time period between the start time of the target positioning of the subject and the start time of the radiation operation. In some embodiments, the plurality of reference images and the reference physiological motion information may be acquired during a time period between the end time of the target positioning of the subject and the start time of the radiation operation. In some embodiments, the plurality of reference images of the target may be acquired by an imaging device online before the radiation operation during the radiation period. As used herein, "an image of a subject acquired by a device online" refers to that the image is acquired by scanning the subject using the device during the radiation period.

In 420, the processing device 120 (e.g., the establishing module 320) may establish a correlation model based on the plurality of reference images and the reference physiological motion information.

In some embodiments, the processing device 120 establish the correlation model based on the time information of the plurality of reference images and the time information of the reference physiological motion information. For example, the processing device 120 may establish the correlation model by correlating reference image(s) with the reference physiological motion information that are acquired at a same time point (or during a same time period).

The correlation model may reflect a relationship between the plurality of reference images and phases of the reference physiological motion information respectively. For example, the correlation model may include a relationship among a plurality of respiratory phases (e.g., an inspiration phase, an expiration phase), reference image(s) corresponding to each of the plurality of respiratory phases, and/or reference image feature(s) corresponding to each of the plurality of respiratory phases.

In some embodiments, the reference images may be 3D images. For each of the plurality of 3D reference images, the processing device 120 may generate a plurality of 2D images corresponding to a plurality of gantry angles respectively based on the 3D reference image. The 2D images may be used to determine the reference image features related to the physiological motion of the subject (i.e., there is no need to acquire the reference physiological motion by the detection device 150). For example, for each 3D reference image, the processing device 120 may generate a plurality of digitally reconstructed radiograph (DRR) images based on the 3D reference image according to one or more DRR generation algorithms (e.g., cylindrical harmonics, reassembling previously generated projection blocks). As used herein, a DRR image refers to a simulated radiographic image produced through a perspective projection of a 3D image onto a 2D image plane. Further, the processing device 120 may extract reference image features (e.g., diaphragm features) of the subject in the DRR images. As described in connection with above, the reference image features (e.g., the diaphragm features) of the subject in the DRR images may correspond to a plurality of respiratory phases. Furthermore, the processing device 120 may establish the correlation model based on the plurality of DRR images, a plurality of gantry angles corresponding to the plurality of DRR images respectively, and the reference image features (e.g., the diaphragm features) of the subject in the DRR images. For example, the correlation model may include a plurality of respiratory phases, reference image feature(s) corresponding to each of the plurality of respiratory phases, DRR image(s) corresponding to each of the plurality of respiratory phases, and gantry angles corresponding to the DRR images.

In 430, the processing device 120 (e.g., the monitoring module 330) may monitor real-time motion information of the target based on the correlation model during the radiation operation performed during the radiation period.

In some embodiments, during the radiation operation (e.g., a radiotherapy treatment operation), a radiation source (e.g., the treatment radiation source 1111) of a medical device (e.g., the treatment device 111) may generate and emit a radiation beam toward the subject for treatment.

In some embodiments, the real-time motion information may include a position, a motion frequency, a motion amplitude, a motion direction, or the like, or any combination thereof.

In some embodiments, the processing device 120 may obtain a target image of the subject acquired during the radiation operation and corresponding target physiological motion information of the subject. The processing device 120 may determine a target phase based on the target physiological motion information. The processing device 120 may obtain a target reference image based on the target phase and the correlation model. Then the processing device 120 may monitor the real-time motion information of the target by comparing the target reference image and the target image. More descriptions for monitoring the real-time motion information of the target may be found elsewhere in the present disclosure (e.g., FIG. 6 and descriptions thereof).

In some embodiments, as described above, for the fractionated radiation therapy, the processing device 120 may establish corresponding correlation models for the fractions of the fractionated radiation therapy respectively. For example, for each fraction of the fractionated radiation therapy, the processing device 120 may establish a correlation model based on a plurality of reference images and reference physiological motion information acquired in a radiation period of the fraction. The processing device 120 may monitor real-time motion information of the target based on the correlation model during a radiation operation performed during the radiation period of the fraction.

In some embodiments, the processing device 120 may adjust the radiation plan based on the monitored motion information of the target in real time. For example, the processing device 120 may adjust a direction and/or a shape of a radiation beam generated by a treatment radiation source (e.g., the treatment radiation source 1111) of a medical device (e.g., the medical device 110) based on a motion direction and/or a motion amplitude of the target.

In some embodiments, the processing device 120 may determine whether the motion frequency (or the motion amplitude) of the target is greater than a frequency threshold (or an amplitude threshold). In response to determining that the motion frequency (or the motion amplitude) of the target is greater than the frequency threshold (or the amplitude threshold), the processing device 120 may generate a reminder (e.g., a reminder indicating that a re-register between the plan image and the positioning reference image is needed). In some embodiments, in response to determining that the motion frequency (or the motion amplitude) of the target is greater than the frequency threshold (or the amplitude threshold), the processing device 120 may cause the medical device to terminate a scan of the subject. For example, a position of the scanning table that supports the subject may be adjusted based on the monitored motion information of the target, such that the target of the subject is positioned at a treatment isocenter of a medical device (e.g., the treatment device 111). In some embodiments, the processing device 120 may generate an image based on the scan. Then, the processing device 120 may perform a motion artifact correction on the image of the subject based on the monitored motion information.

According to some embodiments of the present disclosure, the correlation model may be established based on the plurality of reference images and the reference physiological motion information acquired in the radiation period. Further, the real-time motion information of the target may be monitored based on the correlation model during the radiation operation. That is, the correlation model may be established based on data and/or information (e.g., the plurality of reference images, the reference physiological motion information) that is acquired shortly before the radiation operation (e.g., several minutes or hours before the radiation operation), accordingly, the correlation model can (substantially) reflect the relationship between feature information of the target of the subject and phases of the physiological motion of the subject during the radiation operation. For example, for a specific fraction of a fractionated radiation therapy, the processing device 120 may generate the correlation model based on the plurality of reference images and the reference physiological motion information acquired in a radiation period of the specific fraction, instead of images and physiological motion information acquired before the radiation period of the specific fraction (e.g., in a radiation period of a fraction prior to the specific fraction).

In addition, since the acquisition of the plurality of reference images and the reference physiological motion information and the real-time monitoring of the subject are located at a same radiation period, position information of the subject (e.g., a relative position between the subject and the scanning table) during the acquisition of the plurality of reference images and the reference physiological motion information is (substantially) the same as position information of the subject during the radiation operation, which can also improve the monitoring accuracy of the motion information of the target.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, before operation 410, a process for registering the plan image and the positioning reference image, and a process for target positioning of the subject based on the registration result may be added.

In some embodiments, before operation 430, the processing device 120 may determine whether the radiation plan needs to be adjusted based on the plurality of reference images and/or the positioning reference image. In some embodiments, the processing device 120 may determine a predicted dose distribution of the subject based on the plurality of reference images and a plurality of scanning parameters in the radiation plan. For example, the processing device 120 may outline the target of the subject based on the plurality of reference images and/or the positioning reference image. The processing device 120 may determine the predicted dose distribution of the subject based on an outlined target and the radiation plan. Further, the processing device 120 may determine whether the radiation plan needs to be adjusted based on the predicted dose distribution of the subject and a planned dose distribution of the subject. In response to determining that a difference between the predicted dose distribution of the subject and the planned dose distribution of the subject is greater than a dose threshold, the processing device 120 may adjust the radiation plan.

In some embodiments, the generation of the correlation model may be performed offline. In some embodiments, a correlation model library having a plurality of reference correlation models may be previously generated and stored in a storage device (e.g., the storage device 130, the storage device 220, an external storage device). The processing device 120 may select the correlation model of the subject from the correlation model library based on feature information (e.g., the age, the gender, the body shape) of the subject. For example, the processing device 120 may select a reference correlation model of a reference subject having the same feature as or a similar feature to the subject from the correlation model library as the correlation model of the subject. By generating the correlation model library in advance, the generation process of the correlation model may be simplified, which in turn, may improve the efficiency of the generation of the correlation model of the subject.

Figure 5:
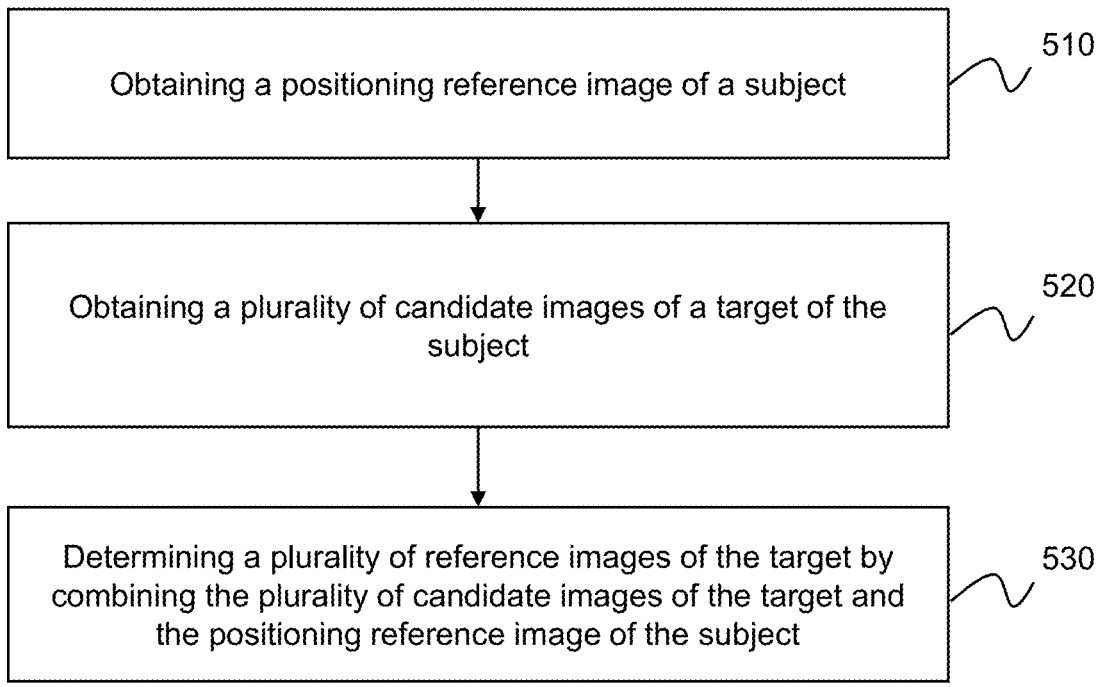
FIG. 5 is a flowchart illustrating an exemplary process for obtaining a plurality of reference images of a target of a subject according to some embodiments of the present disclosure.

FIG. 5 is a flowchart illustrating an exemplary process for obtaining a plurality of reference images of a target of a subject according to some embodiments of the present disclosure. In some embodiments, process 500 may be executed by the medical system 100. For example, the process 500 may be implemented as a set of instructions (e.g., an application) stored in a storage device (e.g., the storage device 130, the storage 220). In some embodiments, the processing device 120 (e.g., the processor 210 of the computing device 200, and/or one or more modules illustrated in FIG. 3) may execute the set of instructions and may accordingly be directed to perform the process 500.

In 510, the processing device 120 (e.g., the first obtaining module 310) may obtain a positioning reference image of a subject.

In some embodiments, the positioning reference image may be used for positioning the subject before a radiation operation is performed on the subject during the radiation period. For example, the positioning reference image may be acquired by a medical device (e.g., the imaging device 112 of the medical device 110) before the radiation operation in the radiation period. As another example, the positioning reference image may be acquired by the medical device before the radiation period.

In some embodiments, a scan range of the positioning reference image may be relatively large, in order to improve the accuracy of subject positioning. For example, the scan range of the positioning reference image may cover a target of the subject. As another example, the scan range of the positioning reference image may cover the entire body of the subject.

In some embodiments, the positioning reference image may include a CT image, an MRI image, a PET image, a PET-CT image, an SPECT-MRI image, etc. In some embodiments, the positioning reference image may include a 2D image, a 3D image, a 4D image, etc.

In some embodiments, the processing device 120 may obtain the positioning reference image from one or more components (e.g., the medical device 110, the terminal 140, the storage device 130) of the medical system 100 or an external storage device via the network 160. For example, the medical device 110 may transmit the positioning reference image to the storage device 130 or any other storage device for storage. The processing device 120 may obtain the positioning reference image from the storage device 130, or any other storage device. As another example, the processing device 120 may obtain the positioning reference image from the medical device 110 directly.

In 520, the processing device 120 (e.g., the first obtaining module 310) may obtain a plurality of candidate images of a target of the subject.

In some embodiments, the plurality of candidate images may be acquired by a medical device (e.g., the imaging device 112 of the medical device 110) before the radiation operation in the radiation period. In some embodiments, a scan range of each candidate image of the plurality of candidate images may be relatively small, in order to prevent the subject from receiving unnecessary radiation. For example, the scan range of the candidate image may cover at least part of the target of the subject. In some embodiments, the plurality of candidate images may correspond to different time points (or time periods) in the radiation period.

In some embodiments, the candidate image may include a CT image, an MRI image, a PET image, a PET-CT image, an SPECT-MRI image, etc. In some embodiments, a modality of the positioning reference image may be the same as a modality of the candidate image. For example, the positioning reference image and the plurality of candidate images may both be CT images. In some embodiments, the candidate image may include a 2D image, a 3D image, a 4D image, etc.

In 530, the processing device 120 (e.g., the first obtaining module 310) may determine a plurality of reference images of the target by combining the plurality of candidate images of the target and the positioning reference image of the subject.

In some embodiments, for each candidate image of the plurality of candidate images, the processing device 120 may generate a reference image based on the candidate image and the positioning reference image. For example, the processing device 120 may generate the reference image based on the candidate image and the positioning reference image by combining the candidate image and the positioning reference image according to one or more algorithms used in image fusion (e.g., an image fusion algorithm, an image interpolation algorithm, an image registration algorithm).

For illustration purposes, the positioning reference image may be a 3D image of the subject. The plurality of candidate images may be 3D images of the target of the subject acquired at different time points during the radiation period. The processing device 120 may generate a 4D image (i.e., a plurality of 3D reference images) by combining the plurality of 3D candidate images of the target and the 3D positioning reference image of the subject.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
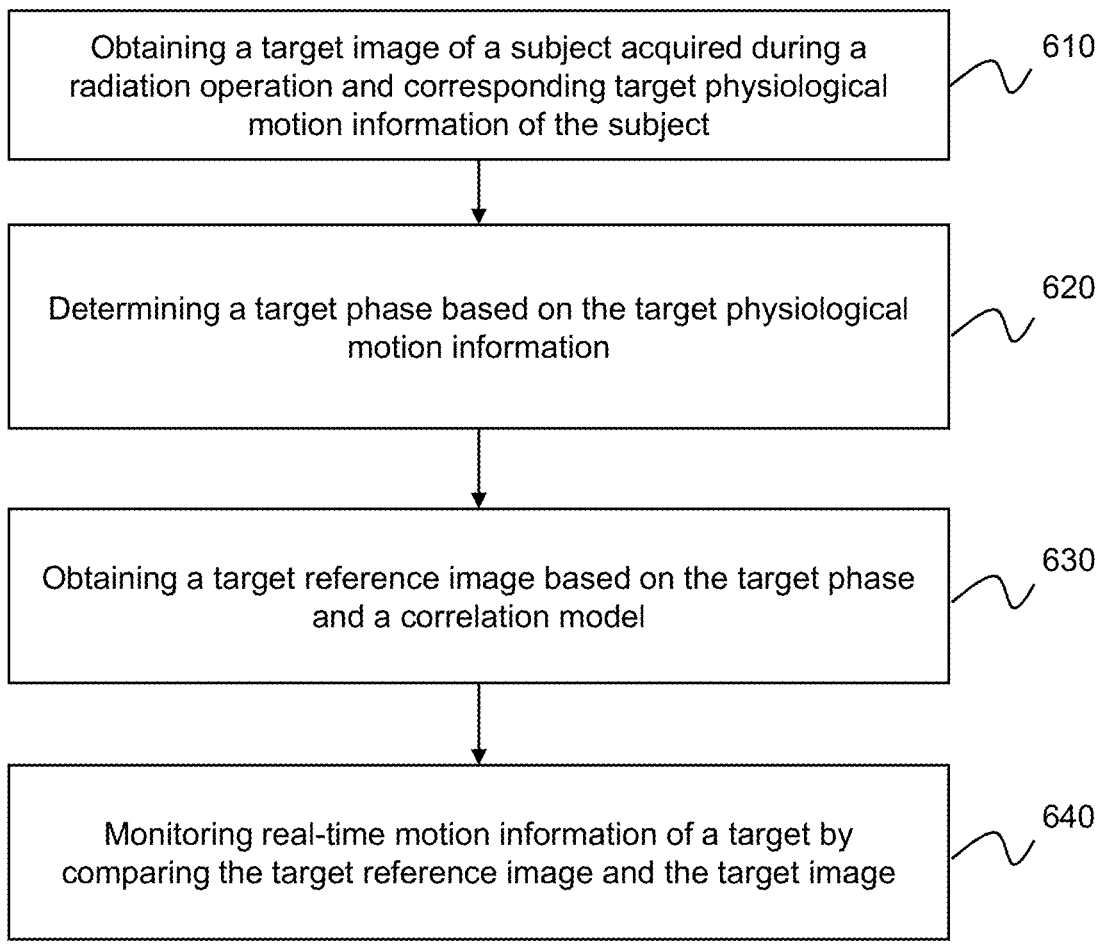
FIG. 6 is a flowchart illustrating an exemplary process for monitoring real-time motion information of a target of a subject according to some embodiments of the present disclosure.

FIG. 6 is a flowchart illustrating an exemplary process for monitoring real-time motion information of a target of a subject according to some embodiments of the present disclosure. In some embodiments, process 600 may be executed by the medical system 100. For example, the process 600 may be implemented as a set of instructions (e.g., an application) stored in a storage device (e.g., the storage device 130, the storage 220). In some embodiments, the processing device 120 (e.g., the processor 210 of the computing device 200, and/or one or more modules illustrated in FIG. 3) may execute the set of instructions and may accordingly be directed to perform the process 600.

In 610, the processing device 120 (e.g., the monitoring module 330) may obtain a target image of a subject acquired during a radiation operation and corresponding target physiological motion information of the subject.

In some embodiments, the target image may include a CT image, an MRI image, a PET image, a PET-CT image, an SPECT-MRI image, etc. In some embodiments, the target image may include a 2D image, a 3D image, etc. For example, the target image may be a 2D X-ray image acquired by a DR device. As another example, the target image may be an EPID image acquired by an EPID of a medical device (e.g., the medical device 110).

In some embodiments, the processing device 120 may obtain an original image of the subject acquired by the medical device during the radiation operation. A scan range of the original image may be relatively small, in order to reduce the radiation time and the radiation dose received by the subject. For example, the scan range of the original image may cover at least part of the target of the subject. The processing device 120 may generate the target image by combining the original image and a positioning reference image of the subject as described in connection with operation 510 (or a plurality of reference images of the subject as described in connection with operation 410).

In some embodiments, the target physiological motion information may include a target physiological motion signal (e.g., a target respiratory signal). In some embodiments, the target respiratory signal may include a respiratory amplitude, a respiratory frequency, or the like, of at least one position on the subject. In some embodiments, the target image and the target physiological motion signal may be acquired at a same time point during the radiation operation. For example, when the target image is acquired during the radiation operation, the detection device 150 may acquire the target respiratory signal of the subject simultaneously.

In some embodiments, the target physiological motion information may include a target image feature related to the physiological motion of the subject. For example, the target physiological motion information may include a target image feature of a diaphragm of the subject. In some embodiments, the processing device 120 may determine the target image feature related to the physiological motion of the subject based on the target image according to an image analysis algorithm (e.g., an image segmentation algorithm, a feature point extraction algorithm).

In some embodiments, a type of the target physiological motion information may be the same as a type of the reference physiological motion information. For example, the target physiological motion information and the reference physiological motion information may both be physiological motion signals. As another example, the target physiological motion information and the reference physiological motion information may both be image features related to the physiological motion of the subject.

In 620, the processing device 120 (e.g., the monitoring module 330) may determine a target phase based on the target physiological motion information.

In some embodiments, the processing device 120 may determine the target phase based on the target respiratory signal and reference physiological motion information (e.g., a reference respiratory motion curve) obtained in operation 410. For example, the target physiological motion information may include a target respiratory amplitude. The processing device 120 may determine a respiratory phase corresponding to the target respiratory amplitude in the reference respiratory motion curve as the target phase.

In some embodiments, the processing device 120 may determine the target phase based on the target image feature and the correlation model obtained in operation 420. As descried in connection with operation 420, the correlation model may reflect a relationship between a respiratory phase and a reference image feature. For example, the correlation model may include a plurality of respiratory phases (e.g., an inspiration phase, an expiration phase) and reference image feature(s) corresponding to each of the plurality of respiratory phases. The processing device 120 may determine a respiratory phase corresponding to the target image feature in the correlation model as the target phase.

In some embodiments, the target image may be a 2D image. The processing device 120 may obtain a target gantry angle corresponding to the target image. For example, the processing device 120 may obtain a target gantry angle corresponding to the target image from a sensor mounted on a gantry of a medical device. As used herein, a gantry angle corresponding to an image refers to that the image is obtained when a radiation source of a medical device is located at the gantry angle. Further, the processing device 120 may determine the target phase based on the target image feature, the target gantry angle, and the correlation model. For example, the processing device 120 may determine a respiratory phase corresponding to the target image feature and the target gantry angle in the correlation model as the target phase.

In 630, the processing device 120 (e.g., the monitoring module 330) may obtain a target reference image based on the target phase and the correlation model.

In some embodiments, the processing device 120 may select a reference image corresponding to the target phase in the correlation model obtained in operation 420. If the reference image obtained in operation 410 and the target image are both 3D images or 2D images, the processing device 120 may determine the selected reference image as the target reference image.

In some embodiments, if the reference image obtained in operation 410 is a 3D image, and the target image is a 2D image, the processing device 120 may generate a DRR image based on the selected reference image and the target gantry angle corresponding to the target image. Then the processing device 120 may determine the DRR as the target reference image. Alternatively, the processing device 120 may select a DRR image corresponding to the target gantry angle and the target phase in the correlation model. Then the processing device 120 may determine the selected DRR as the target reference image.

In some embodiments, a DRR library may be established based on a plurality of 3D reference images, a plurality of DRR images corresponding to each of the plurality of 3D reference images, and a plurality of gantry angles corresponding to the plurality of DRR images. The processing device 120 may select a DRR image from the DRR library based on the target gantry angle corresponding to the target image and the target phase. Then the processing device 120 may determine the selected DRR as the target reference image.

In 640, the processing device 120 (e.g., the monitoring module 330) may monitor real-time motion information of a target by comparing the target reference image and the target image.

In some embodiments, the processing device 120 may identify first feature information of the target in the target reference image. The processing device 120 may identify second feature information of the target in the target image. Feature information (e.g., the first feature information, the second feature information) of the target may include a size (e.g., a length, a width, a height), a contour, a position, or the like, or a combination thereof. The processing device 120 may monitor the real-time motion information of the target by comparing the first feature information of the target and the second feature information of the target. For example, the processing device 120 may monitor the real-time motion information of the target based on a difference between the first feature information and the second feature information.

In some embodiments, in response to determining that the difference between the first feature information and the second feature information is greater than a difference threshold (e.g., a position distance between a first position of the target in the target reference image and a second position of the target in the target image is greater than a position difference threshold), it may indicate that the quality of radiation therapy treatment of the subject is significantly influenced by the physiological motion of the subject. In this situation, the processing device 120 may generate a reminder. In some embodiments, the reminder may be in the form of text, voice, a picture, a video, a haptic alert, or the like, or any combination thereof.

In some embodiments, the processing device 120 and/or a user (e.g., a doctor) of the medical system 100 may adjust at least one parameter associated with the radiation operation based on the real-time motion information of the target. In some embodiments, the at least one parameter associated with the radiation operation may include a scanning parameter (e.g., a voltage of a radiation source, a current of the radiation source, an exposure time of the scan, a table moving speed, a gantry rotation speed, a field of view (FOV), a distance between the radiation source and a detector), a position parameter of at least one component (e.g., a scanning table, a gantry, a detector, a radiation source) of the medical device, a moving parameter (e.g., a moving speed, a moving distance, a moving direction) of the at least one component of the medical device, or the like, or any combination thereof. For example, the processing device 120 may determine a position offset of the target based on the first position of the target in the target reference image and the second position of the target in the target image. The position offset may include a first offset along a first direction (e.g., an X-axis direction of the coordinate system 170 illustrated in FIG. 1), a second offset along a second direction (e.g., a Y-axis direction of the coordinate system 170 illustrated in FIG. 1), and a third offset along a third direction (e.g., a Z-axis direction of the coordinate system 170 illustrated in FIG. 1). The processing device 120 may adjust the at least one parameter associated with the radiation operation based on position offset, such that an adjusted dose distribution of the subject determined based on adjusted parameter value(s) is consistent with a planned dose distribution.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
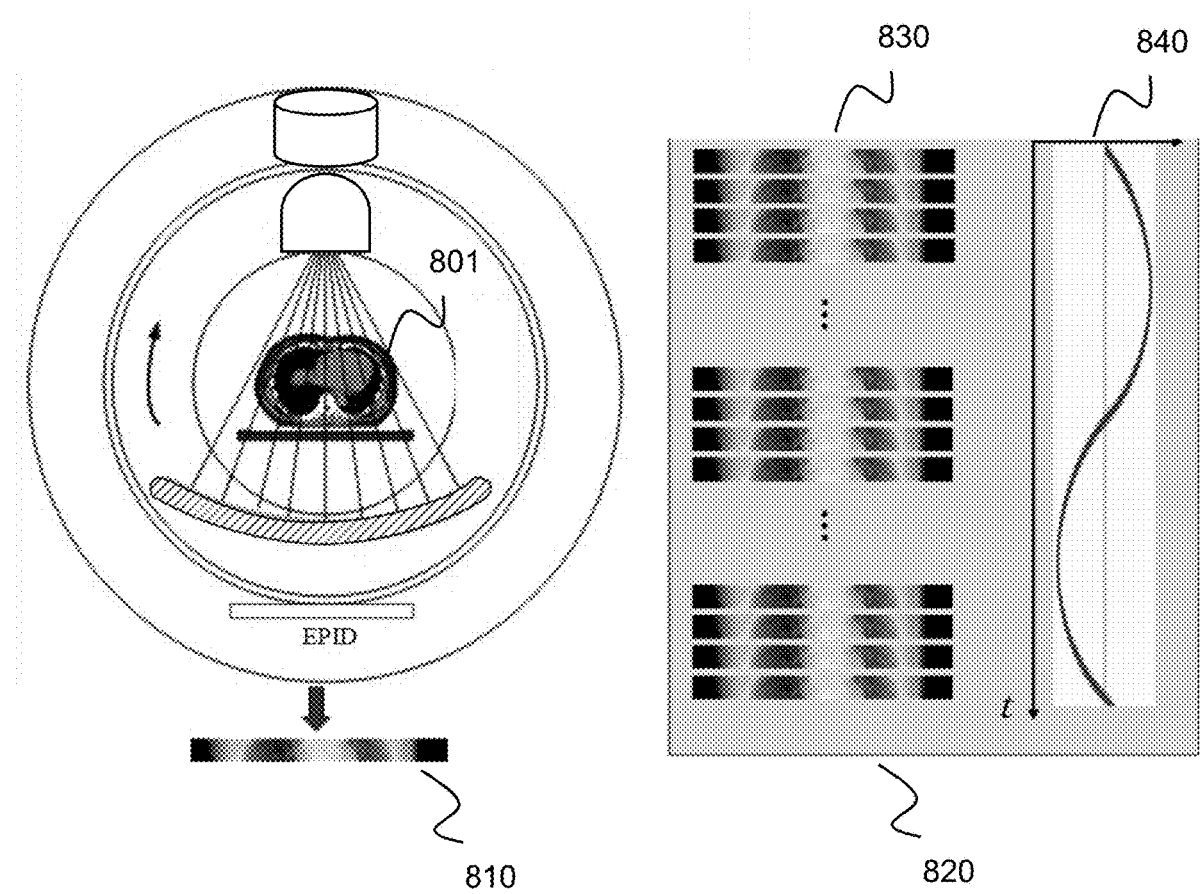
FIG. 8 is a schematic diagram illustrating an exemplary process for monitoring real-time motion information of a target of a subject according to some embodiments of the present disclosure.

FIG. 8 is a schematic diagram illustrating an exemplary process for monitoring real-time motion information of a target of a subject according to some embodiments of the present disclosure.

As illustrated in FIG. 8, the processing device 120 may obtain a target image 810 of a subject 801 acquired by an EPID of a medical device and corresponding target physiological motion information of the subject 801. The processing device 120 may obtain a correlation model 820 reflecting a relationship between a plurality of DRR images 830 and a respiratory motion curve 840. For example, the correlation model 820 may include the respiratory motion curve 840 indicating a plurality of respiratory phases, a plurality of DRR images 830 corresponding to each of the plurality of respiratory phases of the respiratory motion curve 840, and a plurality of gantry angles corresponding to the plurality of DRR images 830. As described in connection with FIG. 6, the processing device 120 may monitor real-time motion information of a target of the subject 801 based on the target image 810, the target physiological motion information, and the correlation model 820. For example, the processing device 120 may monitor the real-time motion information of the target by comparing a first position of the target in the target image 910 and a second position of the target in a target reference image.

Figure 9:
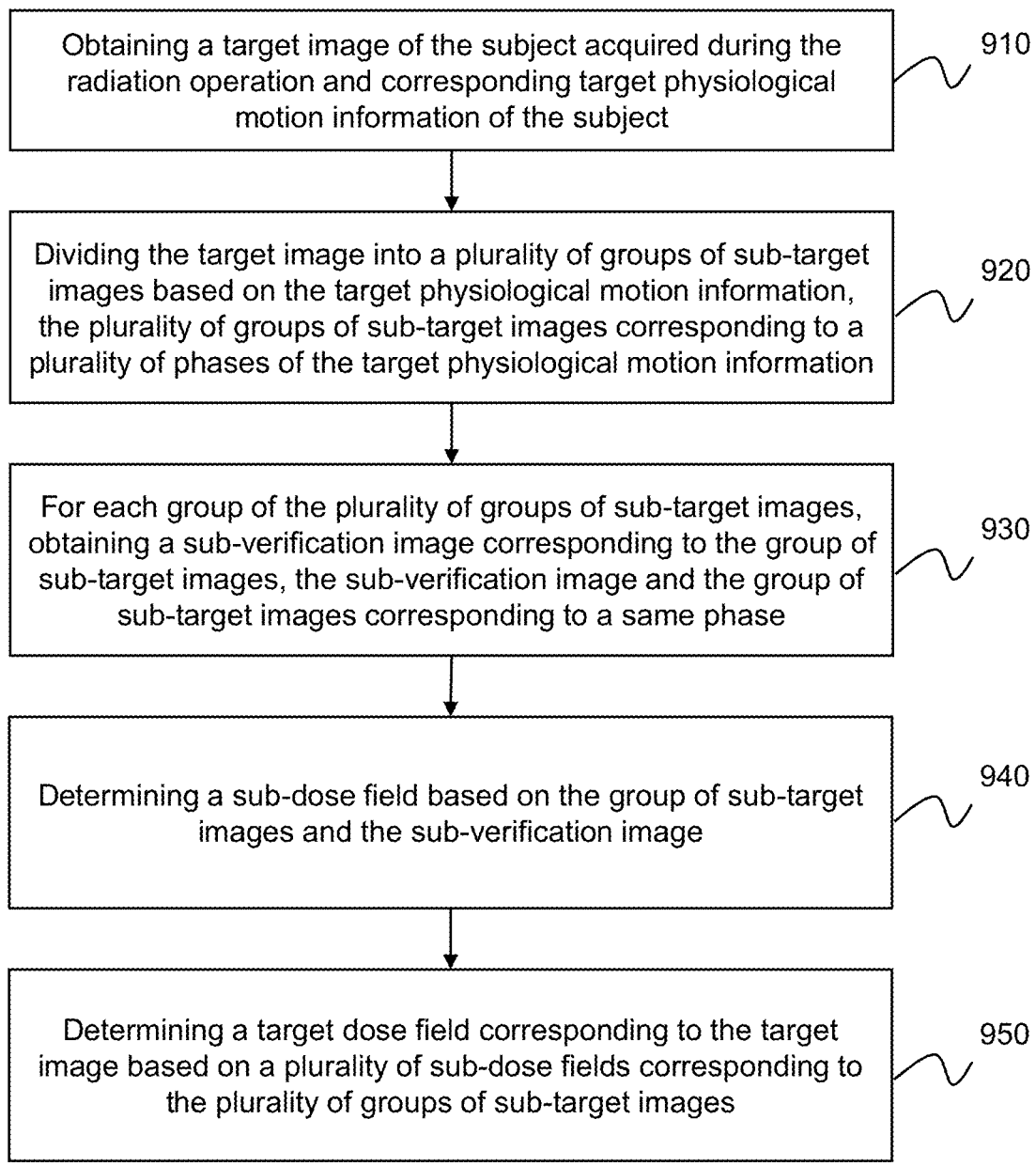
FIG. 9 is a flowchart illustrating an exemplary process for determining a target dose field according to some embodiments of the present disclosure.

FIG. 9 is a flowchart illustrating an exemplary process for determining a target dose field according to some embodiments of the present disclosure. In some embodiments, process 900 may be executed by the medical system 100. For example, the process 900 may be implemented as a set of instructions (e.g., an application) stored in a storage device (e.g., the storage device 130, the storage 220). In some embodiments, the processing device 120 (e.g., the processor 210 of the computing device 200, and/or one or more modules illustrated in FIG. 3) may execute the set of instructions and may accordingly be directed to perform the process 900.

In 910, the processing device 120 (e.g., the second obtaining module 340) may obtain a target image of a subject acquired during a radiation operation and corresponding target physiological motion information of the subject.

In some embodiments, the target image may include a CT image, an MRI image, a PET image, a PET-CT image, an SPECT-MRI image, etc. In some embodiments, the target image may include a 2D image, a 3D image, a 4D image, etc.

In some embodiments, the target image may include time information. In some embodiments, the target image may include a set of images corresponding to a plurality of time points (or time periods) during the radiation operation. For example, the target image may be a 4D CT image including time information. As another example, the target image may include a plurality of 2D images (e.g., EPID images) corresponding to a plurality of time points (or time periods) respectively acquired by an imaging device (e.g., an EPID) of the medical device 110. Merely by way of example, the radiation operation may include a plurality of time periods. The EPID may generate an EPID image based on scan data (e.g., projection data) of the subject acquired in each time period of the plurality of time periods during the radiation operation. Accordingly, the target image may include a set of EPID images corresponding to the plurality of time periods during the radiation operation.

In some embodiments, the target physiological motion information may include a physiological motion signal (e.g., a respiratory signal). The target physiological motion information may correspond to one or more time periods during the radiation operation. In some embodiments, the target image and the target physiological motion signal may be acquired at a same time period during the radiation operation. For example, when the target image is acquired by a medical device during the radiation operation, the detection device 150 may acquire the respiratory signal of the subject simultaneously.

In 920, the processing device 120 (e.g., the dividing module 350) may divide the target image into a plurality of groups of sub-target images based on the target physiological motion information. The plurality of groups of sub-target images may correspond to a plurality of phases of the target physiological motion information.

In some embodiments, the processing device 120 may divide the target image into the plurality of groups of sub-target images based on the time information of the target image and time information of the target physiological motion information. More descriptions for dividing the target image may be found elsewhere in the present disclosure (e.g., FIGS. 10, 11, and descriptions thereof).

In 930, for each group of the plurality of groups of sub-target images, the processing device 120 (e.g., the second obtaining module 340) may obtain a sub-verification image (or a group of sub-verification images) corresponding to the group of sub-target images. The sub-verification image (or the group of sub-verification images) and the group of sub-target images may correspond to a same phase. The group of sub-verification images may include one or more sub-verification images.

In some embodiments, the processing device 120 may obtain the sub-verification image (or the group of sub-verification images) corresponding to the group of sub-target images by dividing a verification image. The verification image may include a treatment planning image, an image acquired before the radiation operation, an image acquired during the radiation operation, etc.

In some embodiments, the treatment planning image may be an image used for positioning the subject before the radiation operation is performed on the subject, or an image used for determining a radiation plan of the subject. In some embodiments, the treatment planning image may be acquired several days (e.g., three days, five days, ten days, fifteen days) before the radiation operation. For example, the treatment planning image may include a plan image, a positioning reference image, etc.

In some embodiments, the image acquired before the radiation operation may be an image used for determine a state of the subject (or a target (e.g., a tumor) of the subject) before the radiation operation. The state of the subject (or a target of the subject) may include a size, a contour, a position, or the like, or a combination thereof. In some embodiments, the image acquired before the radiation operation may be acquired several minutes (e.g., one minute, three minutes, five minutes) before the radiation operation.

In some embodiments, the image acquired during the radiation operation may be an image used for determine the state of the subject (or a target of the subject) during the radiation operation. For example, the image acquired during the radiation operation and the target image may be acquired simultaneously during the radiation operation.

In some embodiments, the verification image may include a CT image, an MRI image, a PET image, a PET-CT image, an SPECT-MRI image, etc. In some embodiments, the verification image may include a 2D image, a 3D image, a 4D image, etc. For example, the verification image may be a 4D CT image.

In some embodiments, the processing device 120 may obtain candidate physiological motion information corresponding to the verification image. For example, when the verification image is acquired by a medical device during the radiation operation, the detection device 150 may acquire the candidate physiological motion information (e.g., a respiratory signal) of the subject simultaneously. Further, the processing device 120 may divide the verification image into a plurality of sub-verification images (or a plurality of groups of sub-verification images) based on the candidate physiological motion information.

In some embodiments, as described in connection with FIG. 4, the verification image or the sub-verification images (or the plurality of groups of sub-verification images) may be the reference images of the subject. For example, the processing device 120 may determine the sub-verification images (or the plurality of groups of sub-verification images) based on a correlation model. As descried in connection with operation 420, the correlation model may include a relationship between a plurality of respiratory phases and reference image(s) corresponding to each of the plurality of respiratory phases. The processing device 120 may determine the one or more reference images corresponding to each of the plurality of respiratory phases as a group of sub-verification images. For example, the processing device 120 may determine one or more reference images corresponding to a phase corresponding to a specific group of sub-target images based on the correlation model as the group of sub-verification images corresponding to the specific group of sub-target images.

In some embodiments, the division of the verification image may be similar to the division of the target image as described in connection with FIGS. 10 and 11, and the detailed descriptions are not repeated here.

In some embodiments, the target image and the verification image may be acquired by a same component or different components of the medical device. For example, the target image and the verification image may be acquired by the imaging device 112 or the EPID of the medical device 110.

In some embodiments, the target physiological motion information and the candidate physiological motion information may be acquired by a same detection device, a same type of detection device, or detection devices with the same information acquisition principle. Accordingly, the accuracy of the division of the verification image based on the candidate physiological motion information and the division of the target image based on the target physiological motion information can be improved, thereby improving the accuracy of radiation dose verification.

In 940, the processing device 120 (e.g., the determination module 360) may determine a sub-dose field based on the group of sub-target images and the sub-verification image (or the group of sub-verification images).

In some embodiments, the processing device 120 may determine the sub-dose field based on the group of sub-target images and the sub-verification image (or the group of sub-verification images) according to a dose reconstruction algorithm. For example, the processing device 120 may determine the sub-dose field by reconstructing scan data corresponding to the group of sub-target images based on the sub-verification image according to one or more dose reconstruction algorithms. The dose reconstruction algorithms may include a point dose reconstruction algorithm, a 2D dose reconstruction algorithm, a 3D dose reconstruction algorithm, etc.

In 950, the processing device 120 (e.g., the determination module 360) may determine a target dose field corresponding to the target image based on a plurality of sub-dose fields corresponding to the plurality of groups of sub-target images.

In some embodiments, the target dose field may reflect an actual radiation dose distribution in a plurality of regions of the subject after the radiation operation is performed on the subject.

In some embodiments, the processing device 120 may determine the target dose field by combining the plurality of sub-dose fields corresponding to the plurality of groups of sub-target images. More descriptions for determining the target dose field may be found elsewhere in the present disclosure (e.g., FIG. 12 and descriptions thereof).

In some embodiments, for each sub-dose field of the plurality of sub-dose fields, the processing device 120 may determine a deformation field by performing a registration operation on the sub-verification image corresponding to the sub-dose field and a preset image. The processing device 120 may determine a deformation sub-dose field based on the sub-dose field and the deformation field. Then the processing device 120 may determine the target dose field by combining a plurality of deformation sub-dose fields corresponding to the plurality of sub-dose fields. More descriptions for determining the target dose field may be found elsewhere in the present disclosure (e.g., FIG. 13 and descriptions thereof).

In some embodiments, the processing device 120 may determine a dose verification result by comparing the target dose field and a plan dose field. The plan dose field may reflect an expected radiation dose distribution in a plurality of regions of the subject after the radiation operation is performed on the subject. The dose verification result may include a difference between the target dose field and the plan dose field, a ratio between the target dose field and the plan dose field, or the like, or any combination thereof. For example, the processing device 120 may determine a difference dose field by subtracting the target dose field from the plan dose field. The difference dose field may reflect a dose difference distribution (between the target dose field and the plan dose field) corresponding to a plurality of regions of the subject after the radiation operation is performed on the subject. In some embodiments, the processing device 120 may confirm or adjust a radiation plan for a subsequent radiation therapy treatment of the subject based on the dose verification result.

According to some embodiments of the present disclosure, the target dose field may be determined based on the target image acquired during the radiation operation and the corresponding target physiological motion information of the subject, which can improve the accuracy of the determination of the target dose field. In addition, the target image and the verification image (which is used for dose verification) may both include time information, and the target image and the verification image may be divided based on the time information and corresponding physiological motion information of the subject. Accordingly, the radiation dose verification methods and systems disclosed herein can improve the accuracy of the radiation dose verification, and facilitate the determination of radiation plan of the subject. Furthermore, the division manner of the target physiological motion information may be determined based on feature information (e.g., a respiratory frequency, respiratory amplitude) of the subject, which can also improve the accuracy of the radiation dose verification.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, as described in connection with FIG. 4, the correlation model may be used in the process for determining the target dose field. Specifically, the processing device 120 may obtain a series of 3D reference images (or 2D reference images) corresponding to different time points (or time periods) and the reference physiological motion information of the subject before the radiation operation during the radiation period. The processing device 120 may generate the correlation model based on the plurality of series of 3D reference images (or 2D reference images) and the reference physiological motion information. The processing device 120 may divide the series of 3D reference images (or 2D reference images) into a plurality of groups of reference images based on the correlation model. The processing device 120 may obtain the target image of the subject acquired during the radiation operation and corresponding target physiological motion information of the subject. The processing device 120 may divide the target image into the plurality of groups of sub-target images based on the target physiological motion information and a plurality of respiratory phases corresponding to the plurality of groups of reference images. For each group of the plurality of groups of sub-target images, the processing device 120 may determine the sub-dose field based on the group of sub-target images and corresponding group of reference images. The processing device may determine the target dose field corresponding to the target image based on the plurality of sub-dose fields corresponding to the plurality of groups of sub-target images.

Figure 10:
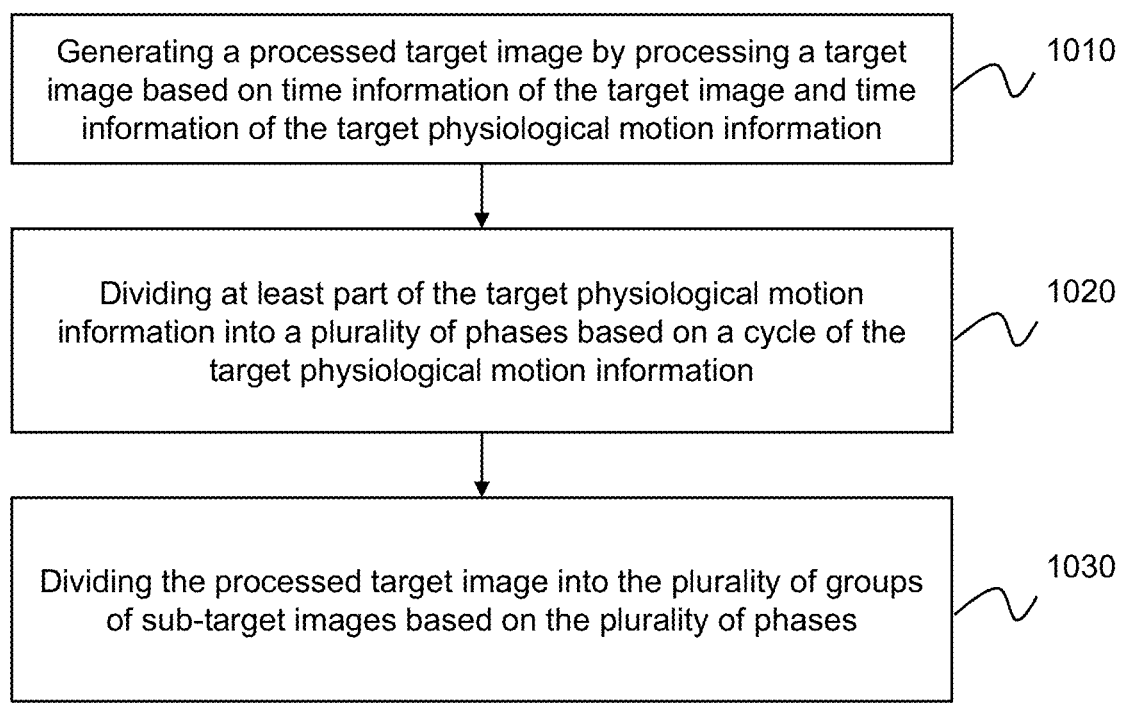
FIG. 10 is a flowchart illustrating an exemplary process for dividing a target image into a plurality of groups of sub-target images according to some embodiments of the present disclosure.

FIG. 10 is a flowchart illustrating an exemplary process for dividing a target image into a plurality of groups of sub-target images according to some embodiments of the present disclosure. In some embodiments, process 1000 may be executed by the medical system 100. For example, the process 1000 may be implemented as a set of instructions (e.g., an application) stored in a storage device (e.g., the storage device 130, the storage 220). In some embodiments, the processing device 120 (e.g., the processor 210 of the computing device 200, and/or one or more modules illustrated in FIG. 3) may execute the set of instructions and may accordingly be directed to perform the process 1000.

In 1010, the processing device 120 (e.g., the dividing module 350) may generate a processed target image by processing a target image based on time information of the target image and time information of the target physiological motion information.

In some embodiments, the processing device 120 may process the target image and the target physiological motion information by correlating the target image with the time information (e.g., time points, time periods) of the target physiological motion information.

In some embodiments, the processing device 120 may process the target image and the target physiological motion information during a data acquisition process (i.e., an acquisition process for acquiring the target image and the target physiological motion information) using software/programs. For example, before a radiation operation, a time stamp of a detection device (e.g., the detection device 150) used to acquire the target physiological motion information and a time stamp of a medical device (e.g., the medical device 110) used to acquire the target image may be set by a same computing device, such that the time stamp of the detection device and the time stamp of the medical device are the same. During the radiation operation, the target image may be acquired by the medical device and the target physiological motion information may be acquired by the detection device simultaneously.

In some embodiments, the processing device 120 may process the target image and the target physiological motion information after the data acquisition process. In some embodiments, the target image may be a 4D CT image including a series of 3D images of the subject corresponding to different time points (or time periods) respectively. The processing device 120 may correlate the 3D images with the time information of the target physiological motion information based on time points (or time periods) corresponding to the 3D images. For example, the processing device 120 may rank the 3D images according to the time information of the target physiological motion information. As another example, the processing device 120 may map the 3D images to one or more time points (or time periods) of a respiratory motion curve based on the time points (or time periods) corresponding to the 3D images. In some embodiments, the processing device 120 may process the target image and the target physiological motion information using a time synchronization module.

In 1020, the processing device 120 (e.g., the dividing module 350) may divide at least part of the target physiological motion information into a plurality of phases based on a cycle of the target physiological motion information.

Taking the target physiological motion information being a respiratory motion curve as an example, a cycle of the respiratory motion curve may be a time interval between two peaks (e.g., two adjacent peak, two non-adjacent peaks), a time interval between two valleys (e.g., two adjacent valleys, two non-adjacent valleys), a time interval between a peak and a valley, etc. In some embodiments, for a same subject, cycles of respiratory motion curves acquired at different times may be substantially the same. In some embodiments, the cycle of the respiratory motion curve may be affected by a plurality of factors, such as, the age, the gender, a body size, a strength of a respiratory muscle, an elasticity of a lung, an elasticity of a thoracic wall of the subject, etc.

Figure 11A:
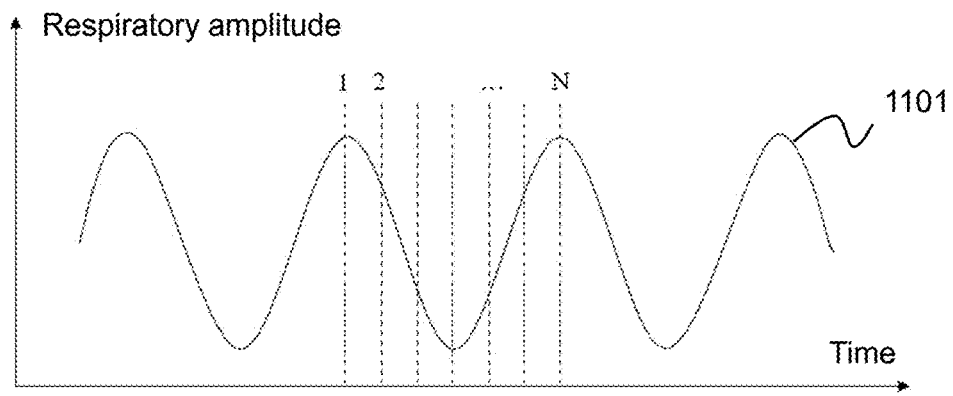
FIGS. 11(A)-(D) are schematic diagrams illustrating exemplary processes for dividing a respiratory motion curve into a plurality of respiratory phases according to some embodiments of the present disclosure.
Figure 11B:
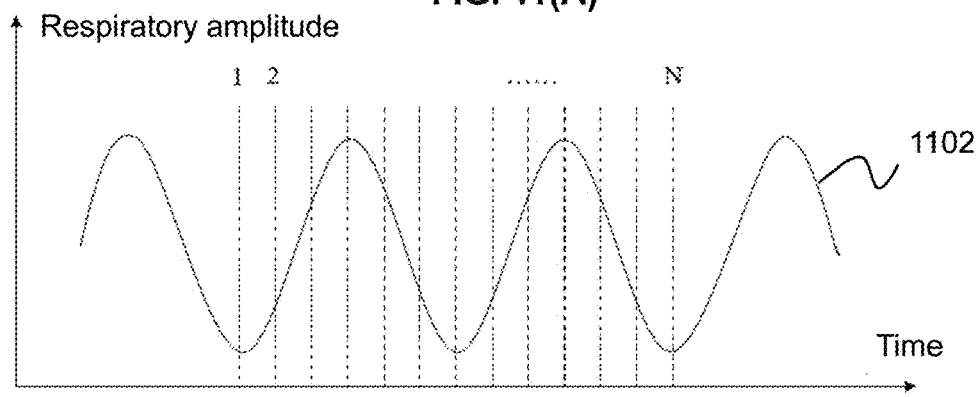
Figure 11C:
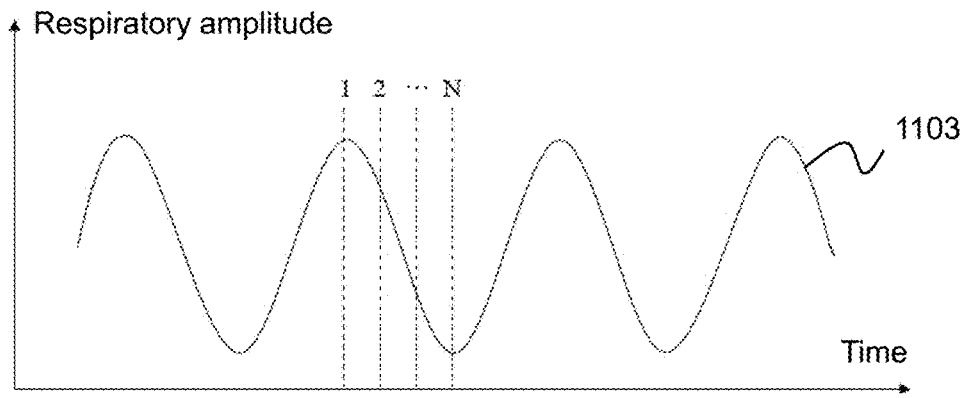
Figure 11D:
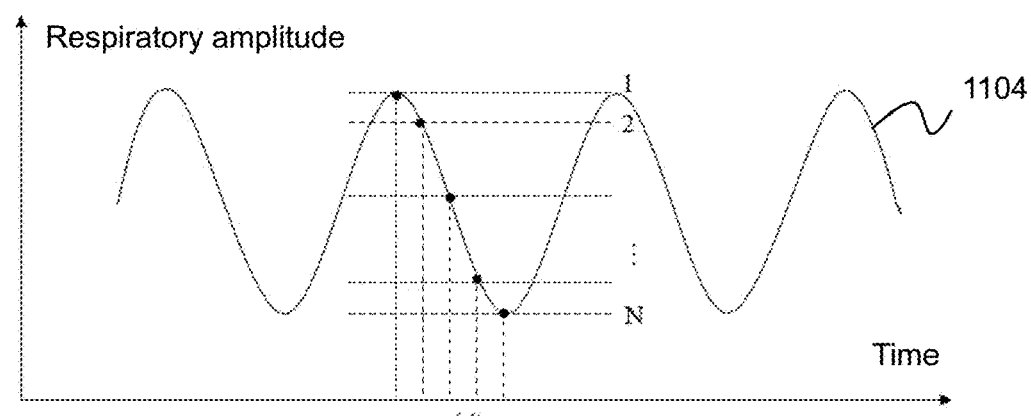

In some embodiments, the processing device 120 may divide at least part of the respiratory motion curve (e.g., a half cycle of the respiratory motion curve, a portion of one or more cycles of the respiratory motion curve) into a plurality of phases based on the cycle of the respiratory motion curve. For example, as illustrated in FIGS. 11(A)-11(C), the processing device 120 may divide the at least part of the respiratory motion curve along a time axis direction of the respiratory motion curve. As another example, as illustrated in FIG. 11(D), the processing device 120 may divide the at least part of the respiratory motion curve along a respiratory amplitude axis direction of the respiratory motion curve.

In some embodiments, the processing device 120 may divide the at least part of the respiratory motion curve uniformly or randomly. For example, the processing device 120 may divide a cycle of the respiratory motion curve into N sections uniformly, wherein time intervals correspond to sections are the same. The N sections may correspond to N respiratory phases (e.g., P1, P2, . . . , PN). Additionally and/or alternatively, the processing device 120 may divide the at least part of the respiratory motion curve according to a predetermined rule. The predetermined rule may be set manually or be determined by one or more components of the medical system 100 according to different situations. For example, the processing device 120 may divide a cycle of the respiratory motion curve into N sections, wherein time intervals corresponding to the N sections may be gradually increase with time.

In some embodiments, a number (or count) of phases and/or a time interval between adjacent phases may be determined based on a respiratory amplitude of the subject. For example, a larger respiratory amplitude may correspond to a larger number (or count) of phases and/or a longer time interval between adjacent phases. In some embodiments, the number (or count) of phases and/or the time interval between adjacent phases may be determined based on a respiratory cycle (a respiratory frequency) of the subject. For example, a shorter respiratory cycle (or higher respiratory frequency) may correspond to a smaller number (or count) of phases and/or a shorter time interval between adjacent phases.

In some embodiments, the number (or count) of phases and/or the time interval between adjacent phases may be determined based on the degree to which the subject (e.g., the target of the subject) is affected by the respiratory motion. For example, if a respiratory frequency of the subject is relatively high (e.g., higher than a frequency threshold) and/or a respiratory cycle of the subject is relatively short (e.g., shorter than a cycle threshold), it may indicate that the position of the target of the subject is influenced by the respiratory motion more frequently. Accordingly, a shorter respiratory cycle (or higher respiratory frequency) may correspond to a larger number (or count) of phases and/or a shorter time interval between adjacent phases. As another example, if a respiratory amplitude of the subject is relatively large (e.g., larger than an amplitude threshold), it may indicate that the position of the target of the subject is significantly influenced by the respiratory motion. Accordingly, a larger respiratory amplitude may correspond to a larger number (or count) of phases and/or a shorter time interval between adjacent phases.

In some embodiments, the number (or count) of phases and/or the time interval between adjacent phases may be determined based on other factors, such as a physical state (e.g., a healthy condition) or a mental state of the subject during the radiation operation.

In 1030, the processing device 120 (e.g., the dividing module 350) may divide the processed target image into the plurality of groups of sub-target images based on the plurality of phases.

In some embodiments, the processing device 120 may divide the processed target image into the plurality of groups of sub-target images based on time periods corresponding to the plurality of phases. Each group of the plurality of groups of sub-target images may correspond to a phase of the plurality of phases. For example, the time period corresponding to the group of sub-target images may be the same as the time period corresponding to the phase.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, operation 1020 may be performed before operation 1010. In some embodiments, operation 1010 may be omitted. The processing device 120 divide the target image based on the time information of the target image and the plurality of phases of the target physiological motion information.

FIGS. 11(A)-(D) are schematic diagrams illustrating exemplary processes for dividing a respiratory motion curve into a plurality of respiratory phases according to some embodiments of the present disclosure.

As illustrated in FIG. 11(A), the processing device 120 may divide a section between two adjacent peaks of a respiratory motion curve 1101 into N phases along a time axis direction of the respiratory motion curve 1101.

As illustrated in FIG. 11(B), the processing device 120 may divide a section between three adjacent valleys of a respiratory motion curve 1102 into N phases along a time axis direction of the respiratory motion curve 1102.

As illustrated in FIG. 11(C), the processing device 120 may divide a section between a peak and an adjacent valley of a respiratory motion curve 1103 into N phases along a time axis direction of the respiratory motion curve 1103.

As illustrated in FIG. 11(C), the processing device 120 may divide a section between a peak and an adjacent valley of a respiratory motion curve 1104 into N phases along a respiratory amplitude axis direction of the respiratory motion curve 1104.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, any part of a respiratory motion curve may be divided into a plurality of phases in any division manner.

Figure 12:
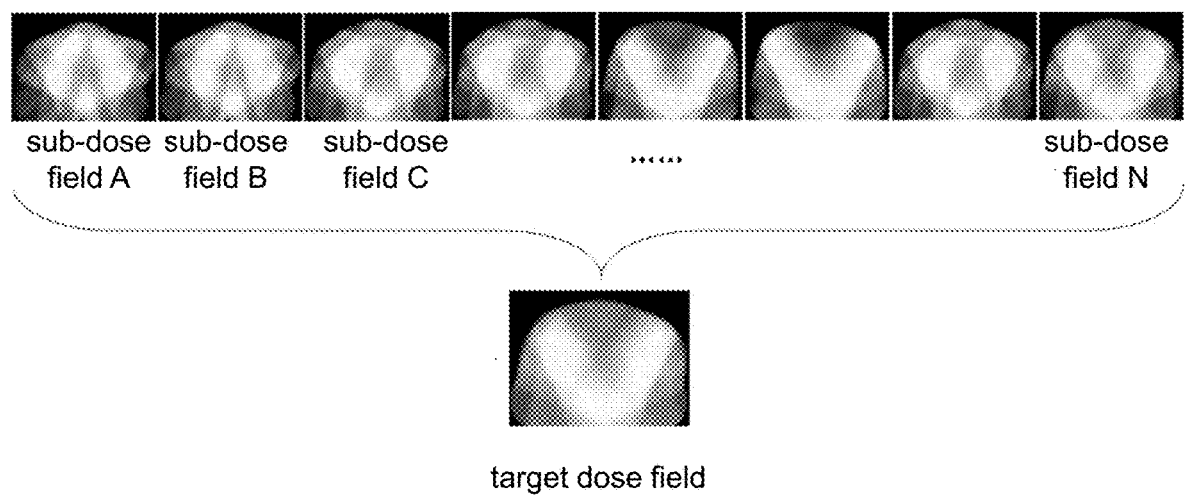
FIG. 12 is a schematic diagram illustrating an exemplary process for determining a target dose field according to some embodiments of the present disclosure.

FIG. 12 is a schematic diagram illustrating an exemplary process for determining a target dose field according to some embodiments of the present disclosure.

As illustrated in FIG. 12, the processing device 120 may determine a plurality of sub-dose fields (e.g., a sub-dose field A, a sub-dose field B, a sub-dose field C, . . . , a sub-dose field N) corresponding to a plurality of groups of sub-target images. The processing device 120 may determine a target dose field by combining the plurality of sub-dose fields. For example, for each element of a plurality of elements in the target dose field, the processing device 120 may determine a sum of values of a plurality of corresponding elements in the plurality of sub-dose field as a value of the element in the target dose field. As used herein, an element of an image refers to a pixel or a voxel of the image.

Figure 13:
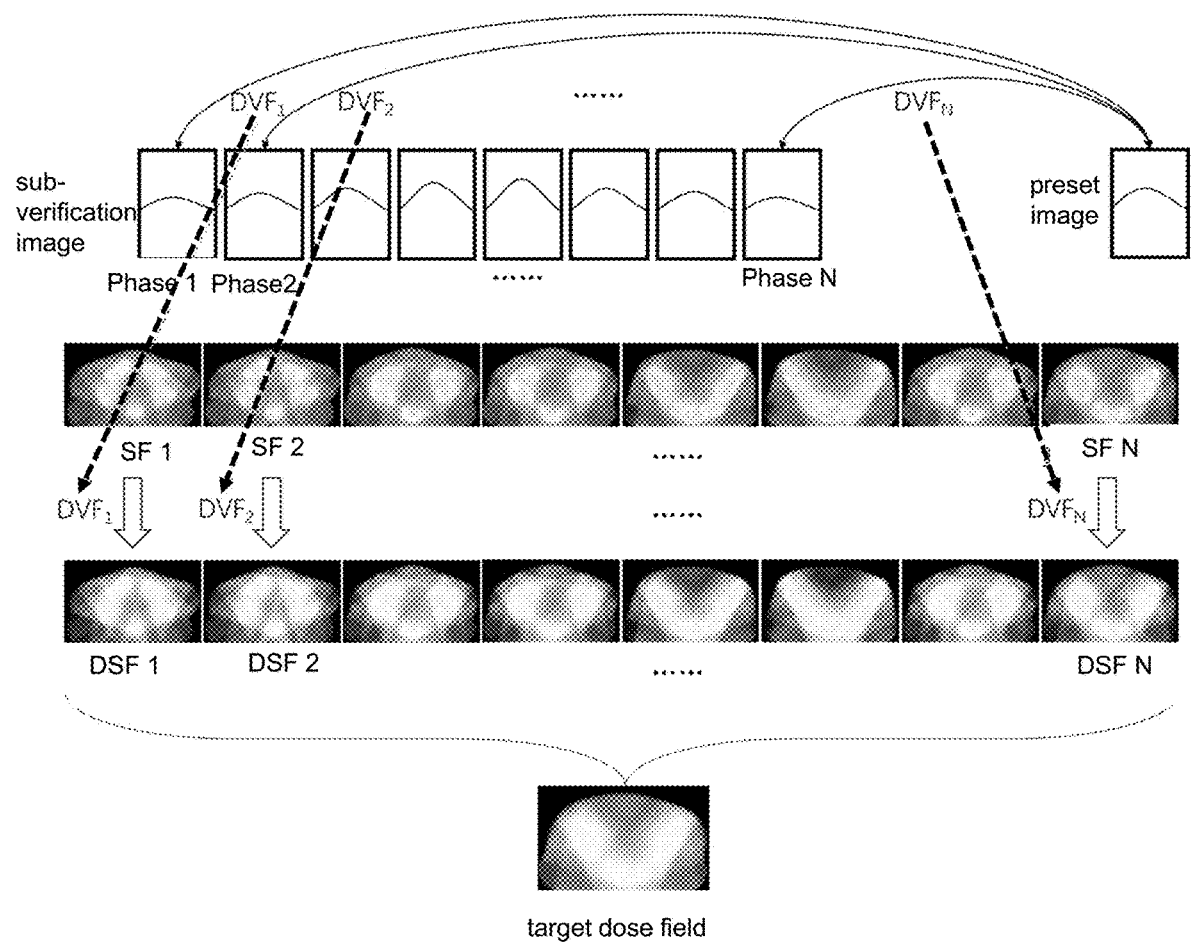
FIG. 13 is a schematic diagram illustrating an exemplary process for determining a target dose field according to some embodiments of the present disclosure.

FIG. 13 is a schematic diagram illustrating an exemplary process for determining a target dose field according to some embodiments of the present disclosure.

As illustrated in FIG. 13, the processing device 120 may obtain a plurality of sub-verification images (e.g., phase 1, phase2, . . . , phase N) corresponding to a plurality of groups of sub-target images. Each sub-verification image and a corresponding group of sub-target images may correspond to a same phase. For each sub-verification image of the plurality of sub-verification images, the processing device 120 may determine a deformation field (e.g., $DVF_1$, $DVF_2$, . . . , $DVF_N$) by performing a registration operation (e.g., a rigid registration operation, a deformable registration operation) on the sub-verification image and a preset image.

In some embodiments, the preset image may include a plan image, a sub-verification image of the plurality of sub-verification images, etc. The plan image may be used to determine a radiation plan of a subject and/or identify/position the subject. In some embodiments, the plan image may be reconstructed based on scan data of the subject. In some embodiments, the plan image may be generated by performing an intensity projection operation (e.g., a maximal intensity projection operation) on a medical image (e.g., a CT image) of the subject.

The deformation field may represent a mapping relationship between a plurality of elements in the sub-verification image and a plurality of elements in the preset image. In some embodiments, the deformation field may include a plurality of vectors each of which corresponds to an element in the sub-verification image. Take a specific vector as an example, a direction of the vector represents a direction in which a corresponding element in the sub-verification image shall move in order to reach a position of a corresponding element in the preset image; a magnitude of the vector represents a distance that the element in the sub-verification image shall travel in the corresponding direction in order to reach the position of the corresponding element in the preset image.

In some embodiments, the processing device 120 may determine the deformation field according to one or more registration algorithms. The registration algorithms may include a radial basis function (e.g., a thin-plate or surface splines transformation, a multiquadric transformation, a compactly-supported transformation), a physical continuum model, a large deformation model (e.g., diffeomorphisms), or the like, or any combination thereof.

Then the processing device 120 may determine a deformation sub-dose field (e.g., $DSF_1$, $DSF_2$, . . . , $DSF_N$) based on a sub-dose field corresponding to the sub-verification image and the deformation field. For example, the processing device 120 may determine the deformation sub-dose field by applying the deformation field on the sub-verification image. Further, the processing device 120 may determine the target dose field by combining a plurality of deformation sub-dose fields (e.g., $DSF_1$, $DSF_2$, . . . , $DSF_N$).

Figure 14:
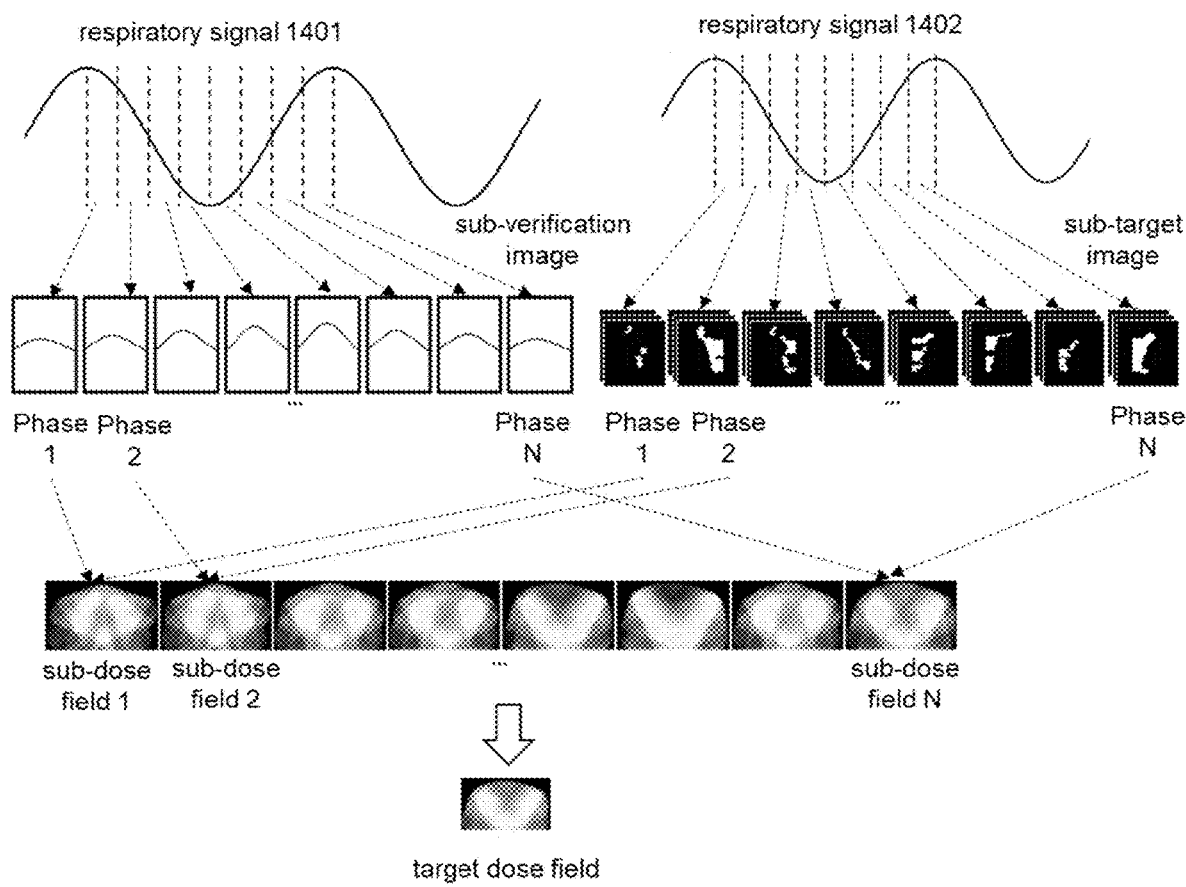
FIG. 14 is a schematic diagram illustrating an exemplary process for radiation dose verification according to some embodiments of the present disclosure.

FIG. 14 is a schematic diagram illustrating an exemplary process for radiation dose verification according to some embodiments of the present disclosure.

As illustrated in FIG. 14, the processing device 120 may obtain a verification image of a subject and a corresponding respiratory signal 1401 of the subject. The processing device

120 may divide the respiratory signal 1401 into a plurality of respiratory phases. The processing device 120 may divide the verification image into a plurality sub-verification images (or a plurality of groups of sub-verification images) (e.g., phase 1, phase 2, . . . , phase N) based on the plurality of respiratory phases of the respiratory signal 1401. Each sub-verification image of the plurality sub-verification images may correspond to a respiratory phase of the plurality of respiratory phases of the respiratory signal 1401.

The processing device 120 may obtain a target image of the subject acquired during a radiation operation and a corresponding respiratory signal 1402 of the subject. The processing device 120 may divide the respiratory signal 1402 into a plurality of respiratory phases. The processing device 120 may divide the target image into a plurality of groups of sub-target images (e.g., phase 1, phase 2, . . . , phase N) based on the plurality of respiratory phases of the respiratory signal 1402. Each sub-target image of the plurality sub-target images may correspond to a respiratory phase of the plurality of respiratory phases of the respiratory signal 1402.

The processing device 120 may determine a plurality of sub-dose fields (e.g., a sub-dose field 1, a sub-dose field 2, . . . , a sub-dose field N) based on the plurality of groups of sub-target images and the plurality sub-verification images (or the plurality of groups of sub-verification images). The processing device 120 may determine a target dose field corresponding to the target image based on the plurality of sub-dose fields.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (e.g., through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation system, comprising:
   at least one storage medium including a set of instructions; and
   at least one processor in communication with the at least one storage medium, wherein when executing the set of instructions, the at least one processor is directed to cause the system to perform operations including:
      obtaining a plurality of reference images of a target of a subject and reference physiological motion information of the subject, wherein the plurality of reference images and the reference physiological motion information are acquired in a radiation period;
      establishing a correlation model based on the plurality of reference images and the reference physiological motion information; and
      monitoring real-time motion information of the target based on the correlation model during a radiation operation performed during the radiation period.

2. The system of claim 1, wherein the obtaining a plurality of reference images of a target of a subject includes:
   obtaining a positioning reference image of the subject;
   obtaining a plurality of candidate images of the target of the subject; and
   determining the plurality of reference images of the target by combining the plurality of candidate images of the target and the positioning reference image of the subject.

3. The system of claim 1, wherein the reference physiological motion information includes a respiratory signal or an image feature related to a respiratory motion of the subject.

4. The system of claim 1, wherein the correlation model reflects a relationship between the plurality of reference images and phases of the reference physiological motion information respectively.

5. The system of claim 1, wherein the monitoring real-time motion information of the target based on the correlation model during a radiation operation performed during the radiation period includes:
   obtaining a target image of the subject acquired during the radiation operation and corresponding target physiological motion information of the subject;
   determining a target phase based on the target physiological motion information;
   obtaining a target reference image based on the target phase and the correlation model; and
   monitoring the real-time motion information of the target by comparing the target reference image and the target image.

6. The system of claim 1, wherein the operations further include:
   adjusting at least one parameter associated with the radiation operation based on the real-time motion information of the target.

7. The system of claim 1, wherein the plurality of reference images of the target are acquired by an imaging device online before the radiation operation, and the plurality of reference images correspond to different time points in the radiation period.

8. The system of claim 1, wherein the operations further include:
   obtaining a target image of the subject acquired during the radiation operation and corresponding target physiological motion information of the subject;
   dividing the target image into a plurality of groups of sub-target images based on the target physiological motion information, the plurality of groups of sub-target images corresponding to a plurality of phases of the target physiological motion information;
   for each group of the plurality of groups of sub-target images,
      obtaining a group of sub-verification images corresponding to the group of sub-target images, the group of sub-verification images and the group of sub-target images corresponding to a same phase; and
      determining a sub-dose field based on the group of sub-target images and the group of sub-verification images; and
   determining a target dose field corresponding to the target image based on a plurality of sub-dose fields corresponding to the plurality of groups of sub-target images.

9. The system of claim 8, wherein the group of sub-verification images corresponding to the group of sub-target images is obtained by dividing a verification image, the verification image including at least one of a treatment planning image, an image acquired before the radiation operation, or an image acquired during the radiation operation.

10. The system of claim 8, wherein the determining a target dose field corresponding to the target image based on a plurality of sub-dose fields corresponding to the plurality of groups of sub-target images includes:
determining the target dose field by combining the plurality of sub-dose fields corresponding to the plurality of groups of sub-target images.

11. The system of claim 8, wherein the determining a target dose field corresponding to the target image based on a plurality of sub-dose fields corresponding to the plurality of groups of sub-target images includes:
for each sub-dose field of the plurality of sub-dose fields,
determining a deformation field by performing an image registration operation on the group of sub-verification images corresponding to the sub-dose field and a preset image; and
determining a deformation sub-dose field based on the sub-dose field and the deformation field; and
determining the target dose field by combining a plurality of deformation sub-dose fields corresponding to the plurality of sub-dose fields.

12. The system of claim 11, wherein the preset image includes a plan image or a sub-verification image of a plurality of groups of sub-verification images corresponding to the plurality of groups of sub-target images.

13. The system of claim 8, wherein the operations further include:
determining a dose verification result by comparing the target dose field and a plan dose field.

14. A radiation system, comprising:
at least one storage medium including a set of instructions; and
at least one processor in communication with the at least one storage medium, wherein when executing the set of instructions, the at least one processor is directed to cause the system to perform operations including:
obtaining a target image of the subject acquired during the radiation operation and corresponding target physiological motion information of the subject;
dividing the target image into a plurality of groups of sub-target images based on the target physiological motion information, the plurality of groups of sub-target images corresponding to a plurality of phases of the target physiological motion information;
for each group of the plurality of groups of sub-target images,
obtaining a group of sub-verification images corresponding to the group of sub-target images, the group of sub-verification images and the group of sub-target images corresponding to a same phase; and
determining a sub-dose field based on the group of sub-target images and the group of sub-verification images; and
determining a target dose field corresponding to the target image based on a plurality of sub-dose fields corresponding to the plurality of groups of sub-target images.

15. The system of claim 14, wherein the obtaining a group of sub-verification images corresponding to the group of sub-target images includes:

obtaining a plurality of reference images of the subject and corresponding reference physiological motion information of the subject;
establishing a correlation model based on the plurality of reference images and the reference physiological motion information; and
obtaining the group of sub-verification images corresponding to the group of sub-target images based on the correlation model.

16. The system of claim 15, wherein the correlation model reflects a relationship between the plurality of reference images and phases of the reference physiological motion information respectively, and the obtaining the group of sub-verification images corresponding to the group of sub-target images based on the correlation model includes:
determining one or more reference images corresponding to a phase corresponding to the group of sub-target images based on the correlation model as the group of sub-verification images corresponding to the group of sub-target images.

17. A radiation method, which is implemented on a computing device including at least one processor and at least one storage device, comprising:
obtaining a plurality of reference images of a target of a subject and reference physiological motion information of the subject, wherein the plurality of reference images and the reference physiological motion information are acquired in a radiation period;
establishing a correlation model based on the plurality of reference images and the reference physiological motion information; and
monitoring real-time motion information of the target based on the correlation model during a radiation operation performed during the radiation period.

18. The method of claim 17, wherein the obtaining a plurality of reference images of a target of a subject includes:
obtaining a positioning reference image of the subject;
obtaining a plurality of candidate images of the target of the subject; and
determining the plurality of reference images of the target by combining the plurality of candidate images of the target and the positioning reference image of the subject.

19. The method of claim 17, wherein the correlation model reflects a relationship between the plurality of reference images and phases of the reference physiological motion information respectively.

20. The method of claim 17, wherein the monitoring real-time motion information of the target based on the correlation model during a radiation operation performed during the radiation period includes:
obtaining a target image of the subject acquired during the radiation operation and corresponding target physiological motion information of the subject;
determining a target phase based on the target physiological motion information;
obtaining a target reference image based on the target phase and the correlation model; and
monitoring the real-time motion information of the target by comparing the target reference image and the target image.

\* \* \* \* \*